US009273027B2

(12) United States Patent
Carroll et al.

(10) Patent No.: US 9,273,027 B2
(45) Date of Patent: Mar. 1, 2016

(54) ARYLPIPERAZINE OPIOID RECEPTOR ANTAGONISTS

(75) Inventors: Frank I. Carroll, Durham, NC (US); Juan P. Cueva, San Diego, CA (US); James B. Thomas, Efland, NC (US); S. Wayne Mascarella, Hillsborough, NC (US); Scott P. Runyon, Hillsborough, NC (US)

(73) Assignee: RESEARCH TRIANGLE INSTITUTE, Research Triangle Park, NC (US)

( * ) Notice: Subject to any disclaimer, the term of this patent is extended or adjusted under 35 U.S.C. 154(b) by 0 days.

(21) Appl. No.: 13/574,179

(22) PCT Filed: Oct. 12, 2010

(86) PCT No.: PCT/US2010/052311
§ 371 (c)(1),
(2), (4) Date: Jul. 19, 2012

(87) PCT Pub. No.: WO2011/106039
PCT Pub. Date: Sep. 1, 2011

(65) Prior Publication Data
US 2012/0295919 A1    Nov. 22, 2012

Related U.S. Application Data

(60) Provisional application No. 61/307,534, filed on Feb. 24, 2010, provisional application No. 61/316,423, filed on Mar. 23, 2010.

(51) Int. Cl.
*A61K 31/495* (2006.01)
*C07D 401/12* (2006.01)
*C07D 241/04* (2006.01)
*C07D 295/096* (2006.01)
*A61K 31/496* (2006.01)

(52) U.S. Cl.
CPC ............ *C07D 401/12* (2013.01); *C07D 241/04* (2013.01); *C07D 295/096* (2013.01); *A61K 31/495* (2013.01); *A61K 31/496* (2013.01)

(58) Field of Classification Search
CPC .. C07D 295/00; C07D 241/04; C07D 401/12; C07D 295/096; A61K 31/495; A61K 31/496
USPC ......................................... 544/384, 385, 403
See application file for complete search history.

(56) References Cited

U.S. PATENT DOCUMENTS

| | | | |
|---|---|---|---|
| 3,170,926 A * | 2/1965 | Fenton et al. ................. 544/392 |
| 4,107,437 A * | 8/1978 | Maffrand et al. ............. 544/376 |
| 5,128,118 A | 7/1992 | Carroll et al. |
| 5,141,959 A | 8/1992 | Carroll et al. |
| 5,298,499 A | 3/1994 | Carroll et al. |
| 5,380,848 A | 1/1995 | Kuhar et al. |
| 5,413,779 A | 5/1995 | Kuhar et al. |
| 5,496,953 A | 3/1996 | Kuhar et al. |
| 5,658,908 A | 8/1997 | Chang et al. |
| 5,736,123 A | 4/1998 | Carroll |
| 5,789,412 A * | 8/1998 | Halazy et al. ............ 514/252.11 |
| 5,831,095 A | 11/1998 | Gonzalez et al. |
| 5,935,953 A | 8/1999 | Kuhar et al. |
| 6,123,917 A | 9/2000 | Carroll |
| 6,262,056 B1 * | 7/2001 | Monge Vega ........ C07D 333/20 514/252.13 |
| 6,329,520 B1 | 12/2001 | Carroll et al. |
| 6,358,492 B1 | 3/2002 | Kuhar et al. |
| 6,416,735 B1 | 7/2002 | Carroll et al. |
| 6,479,509 B1 | 11/2002 | Carroll |
| 6,531,481 B2 | 3/2003 | Carroll et al. |
| 6,531,483 B1 | 3/2003 | Kuhar et al. |
| 6,538,010 B1 | 3/2003 | Carroll |
| 6,552,032 B2 | 4/2003 | Carroll et al. |
| 6,559,159 B2 | 5/2003 | Carroll et al. |
| 6,593,348 B2 | 7/2003 | Carroll et al. |
| 6,706,880 B2 | 3/2004 | Carroll et al. |
| 6,900,228 B1 | 5/2005 | Carroll et al. |
| 6,974,824 B2 * | 12/2005 | Carroll ................. C07D 401/12 514/241 |
| 7,011,813 B2 | 3/2006 | Kuhar et al. |
| 7,189,737 B2 | 3/2007 | Kuhar et al. |
| 7,291,737 B2 | 11/2007 | Kuhar et al. |
| 7,399,762 B2 | 7/2008 | Carroll et al. |
| 7,417,043 B2 * | 8/2008 | Sonesson et al. .............. 514/247 |
| 7,449,466 B2 * | 11/2008 | Takegawa et al. ....... 514/253.01 |
| 7,476,679 B2 | 1/2009 | Carroll et al. |
| 7,615,567 B2 | 11/2009 | Carroll |
| 7,872,023 B2 | 1/2011 | Carroll et al. |
| 8,048,895 B2 * | 11/2011 | Carroll ................. A61K 31/451 514/241 |
| 8,173,678 B2 | 5/2012 | Carroll et al. |

(Continued)

FOREIGN PATENT DOCUMENTS

| | | | |
|---|---|---|---|
| DE | 2456280 A | * | 8/1976 |
| EP | 1 325 912 | | 7/2003 |

(Continued)

OTHER PUBLICATIONS

E. Alexakis et al., 46 Tetrahedron Letters, 4291-4293 (2005).*
D.A. Nelson et al., 36 Journal of Organic Chemistry, 3361-3365 (1971).*
M.N. Romanelli et al., 44 Journal of Medicinal Chemistry, 3946-3955 (2001).*

(Continued)

*Primary Examiner* — Alexander R Pagano
(74) *Attorney, Agent, or Firm* — Oblon, McClelland, Maier & Neustadt, L.L.P.

(57) ABSTRACT

Provided are opioid receptor antagonists represented by the formula (I) where R, $Y_3$, $R_1$, $R_2$, $R_3$, $R_4$ and $R_5$ are as defined herein.

23 Claims, 1 Drawing Sheet

(56) References Cited

U.S. PATENT DOCUMENTS

| | | | |
|---|---|---|---|
| 2002/0132828 A1* | 9/2002 | Carroll | C07D 401/12 514/317 |
| 2002/0137741 A1 | 9/2002 | Desconclois et al. | |
| 2003/0158415 A1 | 8/2003 | Carroll et al. | |
| 2003/0176434 A1 | 9/2003 | Carroll | |
| 2004/0010037 A1* | 1/2004 | Taniguchi et al. | 514/519 |
| 2004/0146518 A1 | 7/2004 | Carroll et al. | |
| 2004/0162282 A1* | 8/2004 | Pennell et al. | 514/218 |
| 2005/0153980 A1* | 7/2005 | Schadt et al. | 514/254.09 |
| 2005/0171061 A1* | 8/2005 | Smith et al. | 514/85 |
| 2006/0106218 A1 | 5/2006 | Pennell et al. | |
| 2006/0205736 A1 | 9/2006 | Noble et al. | |
| 2007/0179155 A1* | 8/2007 | Smith et al. | 514/255.03 |
| 2008/0153870 A1 | 6/2008 | Kuhar et al. | |
| 2008/0214543 A1* | 9/2008 | Taniguchi et al. | 514/235.2 |
| 2009/0054459 A1 | 2/2009 | Schadt et al. | |
| 2009/0163545 A1* | 6/2009 | Goldfarb | 514/312 |
| 2009/0264462 A1* | 10/2009 | Carroll | A61K 31/451 514/307 |
| 2009/0291963 A1 | 11/2009 | Schadt et al. | |
| 2009/0318490 A1 | 12/2009 | Carroll | |
| 2010/0240618 A1* | 9/2010 | Pennell et al. | 514/150 |
| 2011/0015137 A1* | 1/2011 | Cottarel | A61K 45/06 514/21.1 |
| 2011/0183991 A1* | 7/2011 | Pascual-Ramon et al. | 514/252.14 |
| 2012/0178781 A1 | 7/2012 | Carroll et al. | |
| 2013/0158072 A1* | 6/2013 | Carroll | C07D 401/12 514/307 |
| 2015/0005315 A1* | 1/2015 | Carroll | C07D 295/13 514/253.12 |

FOREIGN PATENT DOCUMENTS

| | | |
|---|---|---|
| JP | 49-102693 | 9/1974 |
| JP | 52-148066 | 12/1977 |
| JP | 5-97807 A | 4/1993 |
| JP | 2001-11072 A | 1/2001 |
| JP | 2008-1696 A | 1/2008 |
| WO | WO 93/00313 | 1/1993 |
| WO | WO 01/46145 | 6/2001 |
| WO | WO 0146144 A1 * | 6/2001 |
| WO | WO 02/30896 | 4/2002 |
| WO | WO 03/087086 A2 | 10/2003 |
| WO | WO 03/089410 A1 | 10/2003 |
| WO | WO 2005110989 A1 * | 11/2005 |
| WO | WO 2007/089018 A1 | 8/2007 |
| WO | WO 2009/001127 A1 | 12/2008 |
| WO | WO 2009/128974 | 10/2009 |
| WO | WO 2009/153514 A1 | 12/2009 |
| WO | WO 2010/012817 | 2/2010 |
| WO | WO 2010022055 A2 * | 2/2010 |

OTHER PUBLICATIONS

S. Löber et al., 13 Tetrahedron Asymmetry, 2303-2310 (2002).*
CAPLUS Accession No. 1981:424740, Document No. 95:24740 (May 12, 1984).*
A.K. Saxena et al., 19B Indian Journal of Chemistry, Section B: Organic Chemistry Including Medicinal Chemistry, 873-878 (1980).*
R.E. Mewshaw et al., 8 Bioorganic & Medicinal Chemistry Letters, 295-300 (1998).*
A.G. Koryakovaf et al., 18 Bioorganic & Medicinal Chemistry Letters, 3661-3666 (2008).*
A.H. Sommers et al., 77 Journal of the American Chemical Society, 4171-4172 (1955).*
F.N. Minard et al., 31 Journal of Pharmacy and Pharmacology, 91-93 (1979).*
M. Beller et al., 54 Tetrahedron, 6359-6368 (1998).*
Cas Reg Nos. 416893-07-7 and 415933-74-3.*
CAS Registry No. 1136821-57-2 (Apr. 19, 2009).*
G.L. Regnier et al., 11 Journal of Medicinal Chemistry, 1151-1155 (1968).*
CAS Abstract of Y. Yu et al., 16 Hecheng Huaxue, 277-281 (2008).*
R. Perrone et al., 37 Journal of Medicinal Chemistry, 99-104 (1994).*
A. Arens et al., 4 Khimiko-Farmatsevticheskii Zhurnal, 6-10 (1970).*
CAS Abstract of US2009016345 (2009).*
CAS Registry No. 41592-01-1 (May 15, 2002).*
CAS Registry No. 1 01 9558-15-6 (May 6, 2008).*
CAS Registry No. 1024472-73-8 (Jun. 1, 2008).*
Y. Yu et al., 16 Hecheng Huaxue, 277-281 (2008).*
Extended European Search Report issued Jul. 1, 2013, in European Patent Application No. 10846785.3.
Communication Pursuant to Rules 70(2) and 70a(2) EPC issued Jul. 18, 2013, in European Patent Application No. 10846785.3.
C. B. Pollard, et al., "Derivatives of Piperazine. XXIV. Synthesis of 1-Arylpiperazines and Amino Alcohol Derivatives", Journal of the American Chemical Society, vol. 76, No. 7, XP-007900528, Apr. 5, 1954, pp. 1853-1855.
Maria Novella Romanelli, et al., "Structure-Affinity Relationships of a Unique Nicotinic Ligand: $N^1$-Dimethyl-$N^4$. phenylpiperazinium Iodide (DMPP)" J. Med. Chem., vol. 44. No. 23, XP-002541221,2001, pp. 3946-3955.
Shelly A. Glase, et al., "4-Bromo-1-Methoxy-N[2-(4-Aryl-1-Piperazinyl)Ethyl]-2-Naphthalenecarboxamides: Selective Dopamine D3 Receptor Partial Agonists", Bioorganic & Medicinal Chemistry Letters, vol. 6, No. 12, XP-004134841, 1996, pp. 1361-1366.
Richard E. Mewshaw, et al., "New Generation Dopaminergic Agents. 2. Discovery of 3-OH-Phenoxyethylamine and 3-OH-$N^1$Phenylpiperazine Dopaminergic Templates", Bioorganic & Medicinal Chemistry Letters, vol. 8, No. 3, XP-004136867, 1998, pp. 295-300.
Teruo Komoto, et al., "New μ-Opioid Receptor Agonists with Piperazine Moiety", Chem. Pharm. Bull., vol. 49, No. 10, XP-001180116, 2001, pp. 1314-1320.
F. Ivy Carroll, et al., "1-Substituted 4-(3-Hydroxyphenyl)piperazines Are Pure Opioid Receptor Antagonists", ACS Medicinal Chemistry Letters, vol. 1, No. 7, XP-008143307, Jul. 9, 2010, pp. 365-369.
Matthew D. Metcalf, et al., "Kappa Opioid Antagonists: Past Successes and Future Prospects", The AAPS Journal, vol. 7, No. 3, XP-002437985, 2005, pp. E704-E722.
Jean Jacques Bosc, et al., "2 Amino-2-oxazolines, VII: Influence of Structural Parameters on the Antidepressant Activity of 5-(1-Aryl-4-piperazino)methyl-2-amino-2-oxazolines", Arch. Pharm., vol. 327, No. 3, XP-055067428, 1994, pp. 187-192.
International Search Report Issued Dec. 9, 2010 in PCT/US10/52311 Filed Oct. 12, 2010.
Office Action issued Feb. 13, 2014 in European Patent Application No. 10 846 785.3.
Eric Brenner, et al., "Nickel-catalysed selective N-arylation or N,N'-diarylation of secondary diamines" Tetrahedron, vol. 58, XP004377343, 2002, pp. 6913-6924.
Office Action issued May 8, 2015 in Australian Patent Application No. 2010346633.
Office Action issued May 18, 2015 in Japanese Patent Application No. 2012-554983 (with English language translation).
Chika Kikuchi, et al., "2a-[4-(Tetrahydropyridoindo1-2-yl)butyl] tetrahydrobenzindole Derivatives: New Selective Antagonists of the 5-Hydroxytryptamine$_7$ Receptor", Journal of Medicinal Chemistry, vol. 45, (2002), pp. 2197-2206.
Enza Lacivita, et al., "Determination of 1-aryl-4-propylpiperazine $pK_a$ values: The substituent on aryl modulates basicity", Bioorganic & Medicinal Chemistry, vol. 17, (2009), pp. 1339-1344.
Fredrik Pettersson, et al., Synthesis and Evaluation of a Set of 4-Phenylpiperidines and 4-Phenylpiperazines as D2 Receptor Ligands and the Discovery of the Dopaminergic Stabilizer 4-[3-(Methylsulfonyl)phenyl]-1-propylpiperidine (Huntexil, Pridopidine, ACR16), Journal of Medicinal Chemistry, vol. 53, (2010), pp. 2510-2520.
Susumo Sato, et al., "New μ-Opioid Receptor Agonists with Phenoxyacetic Acid Moiety", Chemical and Pharmaceutical Bulletin, vol. 50, No. 2, (2002), pp. 292-297.

(56) References Cited

OTHER PUBLICATIONS

Nagano Tetsuo, Natsukari Hideaki, Hara Expo Edition, Drug Development Chemistry, Tokyo Chemistry Group, Issue 4, First Edition, (Apr. 10, 2007), pp. 105 to 107.

Bertrand Le Bourdonnec, et al. "Synthesis and Pharmacological Evaluation of Novel Octahydro-1H-pyrido[1,2-a]pyrazine as μ-Opioid Receptor Antagonists", Journal of Medicinal Chemistry, vol. 49, (2006), pp. 7290-7306.

Bertrand Le Bourdonnec, et al. "Synthesis and structure-activity relationships of a new series of 2φ-substituted trans-4,5-dimethyl-4(3-hydroxyphenyl)piperidine as μ-selective opioid antagonists", Bioorganic & Medicinal Chemistry Letters, vol. 16, (2006), pp. 864-868.

Bertrand Le Bourdonnec, et al. "trans-3,4-Dimethyl-4-(3-carboxamidophenyl) piperidines: A Novel Class of μ-Selective Opioid Antagonists", Bioorganic & Medicinal Chemistry Letters, vol. 13, (2003), pp. 4459-4462.

Office Action in corresponding Japanese Application No. 2012-554983, dated Nov. 25, 2015. (w/English Translation).

Journal of American Chemical Society, 1954, 76(7), pp. 1853-1855.

Journal of Medicinal Chemistry, 2001, 44(23), pp. 3946-3955.

Bioorganic & Medicinal Chemistry Letters, 1996, 6(12), pp. 1361-1366.

Chemical Pharmaceutical Bulletin, 2001, 49(10), 1314-1320.

Bioorganic & Medicinal Chemistry Letters, 1998, 8, pp. 295-300.

Office Action in Canadian Patent Application No. 2,787,037, dated Nov. 27, 2015.

Decision of Rejection in Japanese Application No. 2012-554983 with mailing date of Dec. 21, 2015, with English translation.

\* cited by examiner

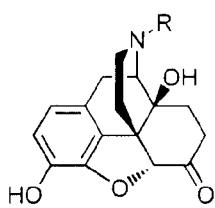
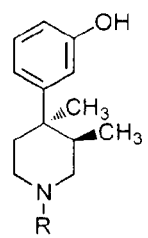
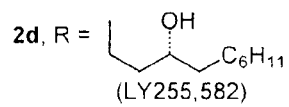
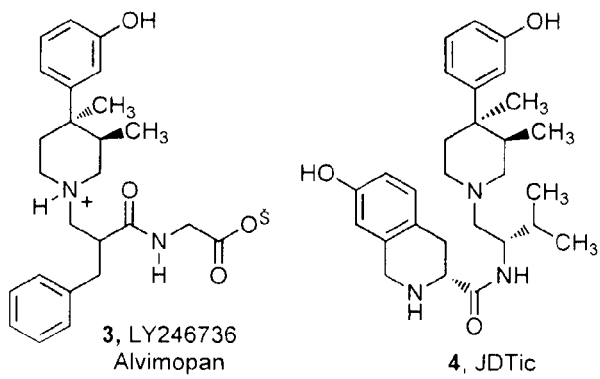
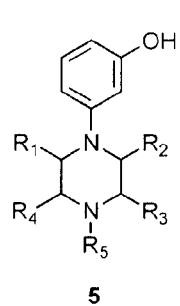
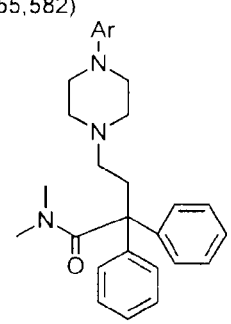
Naloxone (1a), R = CH₂CH=CH₂
Naltrexone (1b), R = CH₂C₃H₅
2a, R = H
2b, R = CH₃
2c, R = C₆H₅(CH₂)₃
2d, R = (LY255,582)
3, LY246736 Alvimopan
4, JDTic
5
6a, Ar = 2-hydroxyphenyl
b, Ar = 3-hydroxyphenyl
c, Ar = 4-hydroxyphenyl
d, Ar = 2-methoxyphenyl
e, Ar = 3-methoxyphenyl
f, Ar = 4-methoxyphenyl

ARYLPIPERAZINE OPIOID RECEPTOR ANTAGONISTS

RELATED APPLICATION INFORMATION

This application claims priority to U.S. provisional application Ser. Nos. 61/307,534, filed on Feb. 24, 2010 and 61/316,423, filed on Mar. 23, 2010, both incorporated herein by reference.

BACKGROUND OF THE INVENTION

1. Field of the Invention

The present invention relates to 4-arylpiperazine compounds. These compounds function as opioid receptor antagonists, and can be used to treat a variety of disease states.

2. Description of the Background

The opioid receptors, μ, δ, κ, and the opioid-like receptor ORL-1 belong to the super family of G-protein coupled receptors (GPCRs) that possess seven helical trans-membrane spanning domains in their architecture.[1] The majority of research efforts focused upon this group of proteins has been directed toward the μ receptor since it mediates the actions of both the opiate and opioid analgesics such as morphine and fentanyl, respectively.[2] However, over the years it has become increasingly clear that the entire family of proteins is actively involved in a host of biological processes.[2] Furthermore, the advent of selective antagonists has demonstrated that pharmacotherapeutic opportunities exist via both negative and positive modulation of this receptor family.[3-8]

The opioid receptor system has been extensively studied, and thousands of compounds have been synthesized and evaluated by in vitro binding and functional assays as well as by animal models.[2] An integral part of the effort to characterize the opioid receptor system has been the discovery of potent, pure antagonists. Naloxone (1a) and naltrexone (1b), both competitive antagonists at μ, δ, and κ opioid receptors,[9] have been extensively used as pharmacological tools to identify and characterize opioid systems (see FIG. 1 for structures). Additionally, naloxone is approved to treat heroin overdose and to reverse respiratory depression caused by morphine.[9] Naltrexone is used to treat heroin and alcohol abuse.

In 1978, Zimmerman and co-workers reported the discovery of a structurally unique series of opioid receptor pure antagonists based on N-substituted analogues of 3,4-dimethyl-4-(3-hydroxyphenyl)piperidine (2a, LY272922).[10] Unlike naloxone (1a) and naltrexone (1b) where the antagonist activity is dependent on the N-allyl or N-cyclopropylmethyl substituent, all N-substituted trans-3,4-dimethyl-4-(3-hydroxyphenyl)piperidines (2) including the N-methyl analogue 2b are opioid receptor pure antagonists.[10-14] A few of the more interesting analogues include alvimopan (3), which is an FDA-approved drug for GI motility disorder,[15] LY255,582 (2d),[13,16] which was developed to treat obesity, and the selective κ opioid receptor antagonist JDTic (4),[6-8,17] which shows activity in rat models of depression,[18] anxiety,[19] and stress-induced cocaine relapse.[18] JDTic appears to be a promising therapeutic.

Komoto et al. reported structures like 6a-f in a paper entitled "New μ-Opioid Receptor Agonists with piperazine Moiety." They do not describe that the compounds have opioid receptor antagonistic efficacy.[20] The compounds are synthesized by a route similar to that used to prepare 5a-j. At present, the opiate class, represented by naloxone (1a), naltrexone (1b), and the N-substituted 3,4-dimethyl-4-(3-hydroxyphenyl)piperidines, represented by alvimopan, LY255,582, and JDTic, are the only two classes of nonpeptide pure opioid receptor antagonists known. The discovery that 3-[4-(substituted piperazine-yl)]phenols (5) as described herein are pure opioid receptor antagonists adds a third example of this important class of compounds.

Studies with selective κ opioid antagonists have shown that this system is intimately involved in brain processes that relate to stress, fear, and anxiety as well as reward-seeking behavior. Studies have shown that JDTic (4) and nor-BNI, another κ opioid selective antagonist, dose-dependently reduce fear and stress-induced responses in multiple behavioral paradigms with rodents (immobility in the forced-swim assay,[18,21] reduction of exploratory behavior in the elevated plus maze, and fear-potentiated startle).[19] Furthermore, selective κ antagonists have been shown to reduce stress-induced reinstatement of cocaine self-administration in rats,[18] to block the stress-induced potentiation of cocaine place preference conditioning,[22-24] to decrease dependence-induced ethanol self-administration,[25] to diminish deprivation-induced eating in rats,[26] and to prevent pre-pulse inhibition mediated by U50,488.[27] These observations regarding the behavioral consequences of receptor blockade in several animal tests suggest that κ antagonists will be useful for treating anxiety, depression, schizophrenia, addiction, and eating disorders.

Previously reported non-selective opioid receptor antagonists such as LY255582 have been found to increase metabolic energy consumption and reduce the weight in obese rats while maintaining muscle mass. These reports suggest that opioid receptor antagonists may be useful in preventing, treating, and/or ameliorating the effect of obesity. Eli Lilly and Company has developed new classes of opioid receptor antagonists that interact with the μ, δ, and κ receptors (termed non-selective) as potential pharmacotherapies to treat obesity and related diseases.[28,29] The Lilly patents suggest that such compounds will be useful for the treatment and/or prophylaxis of obesity and related diseases including eating disorders (bulimia, anorexia nervosa, etc.), diabetes, diabetic complications, diabetic retinopathy, sexual/reproductive disorders, depression, anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, hyperlipoproteinemia, substance abuse, drug overdose, compulsive behavior disorders (such as paw licking in dog), and addictive behaviors such as for example gambling and alcoholism.

SUMMARY OF THE INVENTION

Aryl-substituted piperazines (5) are a new class of opioid receptor antagonists (see the Examples section below for representative structures). Similar to the N-substituted 3,4-dimethyl-4-(3-hydroxyphenyl)piperidines, even the N-methyl substituted analog 5f is a pure opioid antagonist. Changing the N-substituent to an N-phenylpropyl group gives 5b, which has $K_e$ values of 0.88, 13.4, and 4.09 nM at μ, δ, and κ opioid receptors, which are similar to the $K_e$ values of N-phenylpropyl 3,4-dimethyl-4-(3-hydroxyphenyl)piperidine 2c (RTI-5989-264). The JDTic-like analog from this class 5j has $K_e$ values of 22, 274, and 2.7 nM at the μ, δ, and κ opioid receptors, respectively (see Table 1). All compounds of this class thus far synthesized are relatively nonselective opioid receptor antagonists. Thus, their opioid receptor properties are more like those of naloxone (1a), naltrexone (1b), and the originally reported N-substituted 3,4-dimethyl-4-(3-hydroxyphenyl)piperidines.[13]

Thus, the present invention is directed to aryl-substituted piperazine opioid receptor antagonists represented by the formula (I):

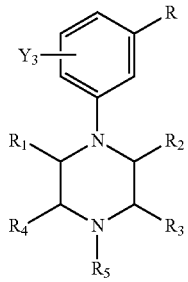

wherein

R is hydrogen, OH, $OC_{1-6}$ alkyl, $C_{1-8}$ alkyl, $C_{1-8}$ haloalkyl, $C_{2-8}$ alkenyl, $C_{2-8}$ alkynyl, aryl substituted by one or more groups $Y_1$, $CH_2$-aryl wherein the aryl group is substituted by one or more groups $Y_1$, $OCOC_{1-8}$ alkyl, $COC_{1-8}$ alkyl, $CONH_2$, NHCHO, $NH_2$, $NHSO_2C_{1-8}$ alkyl, or $NHCO_2C_{1-8}$ alkyl;

$Y_3$ is hydrogen, Br, Cl, F, CN, $CF_3$, $NO_2$, $OR_8$, $CO_2R_9$, $C_{1-6}$ alkyl, $NR_{10}R_{11}$, $NHCOR_{12}$, $NHCO_2R_{12}$, $CONR_{13}R_{14}$ or $CH_2(CH_2)_n Y_2$;

$R_1$, $R_2$, $R_3$ and $R_4$ are each, independently, one of the following structures:

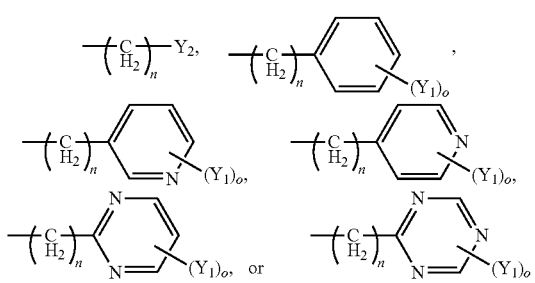

or $R_1$ and $R_2$, $R_2$ and $R_3$ and/or $R_3$ and $R_4$ are bonded together to form a cyclo alkyl group or a bridged heterocyclic ring;

each $Y_1$ is, independently, hydrogen, OH, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_n Y_2$, or two adjacent $Y_1$ groups form a $-O-CH_2-O-$ or $-O-CH_2CH_2-O-$ group;

each $Y_2$ is, independently, hydrogen, $CF_3$, $CO_2R_9$, $C_{1-8}$ alkyl, $NR_{10}R_{11}$, $NHCOR_{12}$, $NHCO_2R_{12}$, $CONR_{13}R_{14}$, $CH_2OH$, $CH_2OR_8$, $COCH_2R_9$,

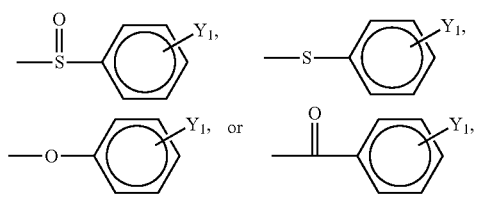

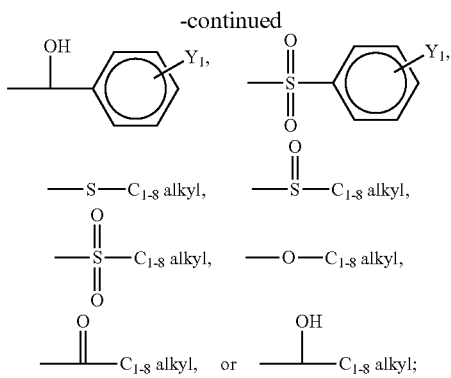

each n is, independently, 0, 1, 2 or 3;
each o is, independently, 0, 1, 2 or 3;
each $R_8$, $R_9$, $R_{10}$, $R_{11}$, $R_{12}$, $R_{13}$ and $R_{14}$ is, independently, hydrogen, $C_{1-8}$ alkyl, $CH_2$-aryl wherein the aryl group is substituted by one or more substituents OH, Br, Cl, F, CN, $CF_3$, $NO_2$, $N_3$, $C_{1-6}$ alkyl, or $CH_2(CH_2)_n Y_2'$;

each $Y_2'$ is, independently, hydrogen, $CF_3$, or $C_{1-6}$ alkyl;

$R_5$ is

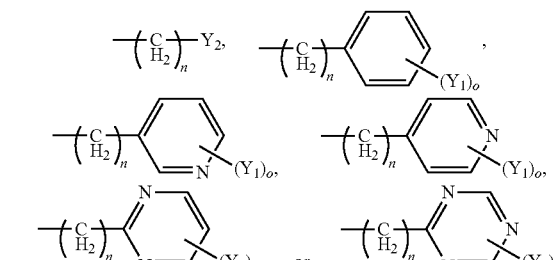

$-CH_2CH_2-X-R_6$, or

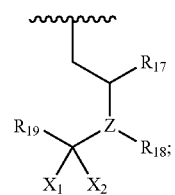

$R_6$ is $C_{1-8}$ alkyl, $C_{2-8}$ alkenyl, $C_{1-4}$ alkyl substituted $C_{4-8}$ cycloalkyl, $C_{1-4}$ alkyl substituted $C_{4-8}$ cycloalkenyl, or thiophene;

X is a single bond, $-C(O)-$ or $-CH(OR_{15})-$;

$R_{15}$ hydrogen, $C_{1-6}$ alkyl, $-(CH_2)_q$-phenyl or $-C(O)-R_{16}$;

$R_{16}$ is $C_{1-4}$ alkyl or $-(CH_2)_q$-phenyl;

each q is, independently, 1, 2 or 3;

$R_{17}$ is hydrogen, $C_{1-8}$ alkyl, $CO_2C_{1-8}$ alkylaryl substituted by one or more groups $Y_1$, $CH_2$-aryl substituted by one or more groups $Y_1$, or $CO_2C_{1-8}$ alkyl;

$R_{18}$ is hydrogen, $C_{1-8}$ alkyl, $C_{2-8}$ alkenyl, $C_{3-8}$ alkynyl, $CH_2CO_2C_{1-8}$ alkyl, $CO_2C_{1-8}$ alkyl or $CH_2$-aryl substituted by one or more groups $Y_1$;

$R_{19}$ is a group selected from the group consisting of structures (a)-(p):

(a) 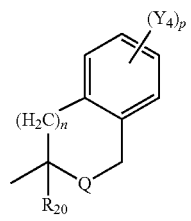
(b) 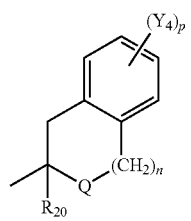
(c) 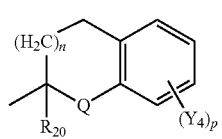
(d) 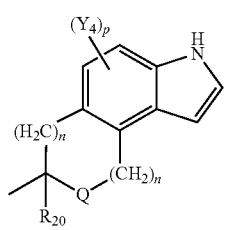
(e) 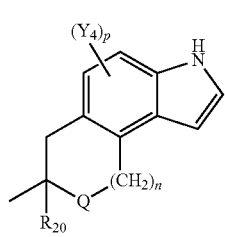
(f) 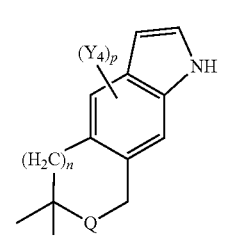
(g) 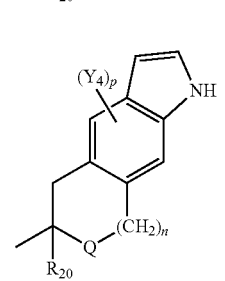
-continued
(h) 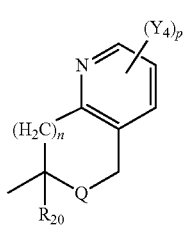
(i) 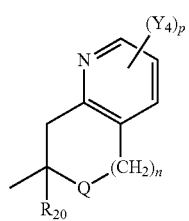
(j) 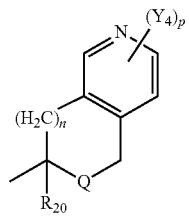
(k) 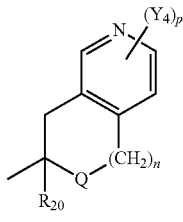
(l) 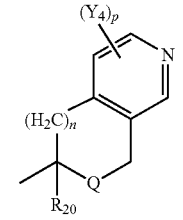
(m) 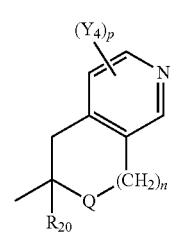
(n) 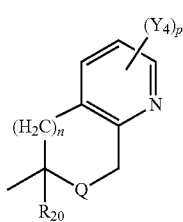

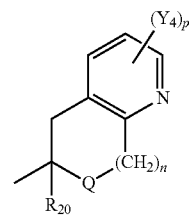
(o)

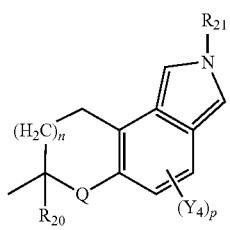
(p)

Q is $NR_{21}$, $CH_2$, O, S, SO, or $SO_2$;

each $Y_4$ is, independently, Br, Cl, F, CN, $CF_3$, $NO_2$, $N_3$, $OR_{22}$, $CO_2R_{23}$, $C_{1-6}$ alkyl, $NR_{24}R_{25}$, $NHCOR_{26}$, $NHCO_2R_{27}$, $CONR_{28}R_{29}$, or $CH_2(CH_2)_nY_2$, or two adjacent $Y_4$ groups form a —O—$CH_2$—O— or —O—$CH_2CH_2$—O— group;

p is 0, 1, 2, or 3;

$R_{20}$ is hydrogen, $C_{1-8}$ alkyl, $C_{2-8}$ alkenyl, $C_{2-8}$ alkenyl, $CH_2OR_{30}$, or $CH_2$-aryl substituted by one or more substituents $Y_1$;

each $R_{21}$ is, independently, hydrogen, $C_{1-8}$ alkyl, $CH_2$-aryl substituted by one or more substituents $Y_1$, $NR_{31}R_{32}$, $NHCOR_{33}$, $NHCO_2R_{34}$, $CONR_{35}R_{36}$, $CH_2(CH_2)_nY_2$, or $C(=NH)NR_{37}R_{38}$, $R_{30}$ is hydrogen $C_{1-8}$ alkyl, $C_{2-8}$ alkenyl, $C_{2-8}$ alkenyl, $CH_2O_2C_{1-8}$ alkyl, $CO_2C_{1-8}$ alkyl, or $CH_2$-aryl substituted by one or more substituents $Y_1$;

$R_{22}$, $R_{23}$, $R_{24}$, $R_{25}$, $R_{26}$, $R_{27}$, $R_{28}$, $R_{29}$, $R_{31}$, $R_{32}$, $R_{33}$, $R_{34}$, $R_{35}$, $R_{36}$, $R_{37}$ and $R_{38}$ are, independently, hydrogen, $C_{1-8}$ alkyl, $CH_2$-aryl substituted by one or more substituents OH, Br, Cl, F, CN, $CF_3$, $NO_2$, $N_3$, $C_{1-6}$ alkyl, or $CH_2(CH_2)_nY_2'$;

Z is N, O or S, wherein when Z is O or S, there is no $R_{18}$;

$X_1$ is hydrogen, $C_{1-8}$ alkyl, $C_{2-8}$ alkenyl, or $C_{2-8}$ alkynyl;

$X_2$ is hydrogen, $C_{1-8}$ alkyl, $C_{2-8}$ alkenyl, or $C_{2-8}$ alkynyl;

or $X_1$ and $X_2$ together form =O, =S, or =NH, with the proviso that when $R_5$ is;

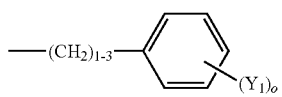

then at least one of $R_1$, $R_2$, $R_3$ and $R_4$ is other than hydrogen as defined above;

or a pharmaceutically acceptable salt thereof.

The present invention also includes pharmaceutical compositions, which comprise the opioid receptor antagonist described above and a pharmaceutically acceptable carrier.

The present invention also includes a method of antagonizing opioid receptors, comprising administering an effective amount of the opioid receptor antagonist discussed above to a subject in need thereof.

The present invention also includes a method of treating drug addiction, drug abuse, depression, anxiety, schizophrenia, obesity and eating disorders, comprising administering an effective amount of the opioid receptor antagonist discussed above to a subject in need thereof.

The present invention also includes a method of treating alcohol addiction, nicotine addiction, cocaine addition and methamphetamine addiction, comprising administering an effective amount of the opioid receptor antagonist discussed above to a subject in need thereof.

The present invention also includes a method of treating diabetes, diabetic complications, diabetic retinopathy, sexual/reproductive disorders, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, hyperlipoproteinemia, substance abuse, drug overdose, compulsive behavior disorders and addictive behaviors, comprising administering an effective amount of the opioid receptor antagonist discussed above to a subject in need thereof.

A more complete appreciation of the invention and many of the attendant advantages thereof will be readily obtained as the same becomes better understood by reference to the following Figures in conjunction with the detailed description below.

BRIEF DESCRIPTION OF THE FIGURES

FIG. 1: chemical structure of compounds 1-6.

DETAILED DESCRIPTION OF THE INVENTION

A broad description of the invention is provided in the Summary section above.

In another embodiment of the invention:

R is hydrogen, OH, $OC_{1-3}$ alkyl, $C_{1-4}$ alkyl, $C_{1-4}$ haloalkyl, $C_{2-4}$ alkenyl, $C_{2-4}$ alkynyl, aryl substituted by one or more groups $Y_1$, $CH_2$-aryl wherein the aryl group is substituted by one or more groups $Y_1$, $OCOC_{1-4}$ alkyl, $COC_{1-4}$ alkyl, $CONH_2$, NHCHO, $NH_2$, $NHSO_2C_{1-4}$ alkyl, or $NHCO_2C_{1-4}$ alkyl; and $Y_3$ is hydrogen, Br, Cl, F, CN, $CF_3$, $NO_2$, $OR_8$, $CO_2R_9$, $C_{1-3}$ alkyl, $NR_{10}R_{11}$, $NHCOR_{12}$, $NHCO_2R_{12}$, $CONR_{13}R_{14}$ or $CH_2(CH_2)_nY_2$;

In another embodiment of the invention, $R_1$, $R_2$, $R_3$ and $R_4$ are each, independently, one of the following structures:

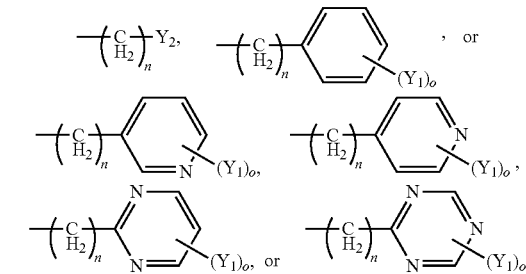

or $R_1$ and $R_2$, $R_2$ and $R_3$ and/or $R_3$ and $R_4$ are bonded together to 5 to 7 membered alkyl group or a bridged heterocyclic ring.

In another embodiment of the invention, $R_5$ is

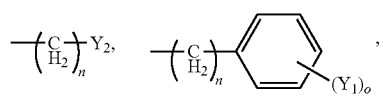

-continued

[chemical structures: $-(CH_2)_n$-pyridinyl-$(Y_1)_o$ variants, pyrimidinyl variants, and]

$$\begin{array}{c} R_{17} \\ | \\ R_{19}-\!\!-\!\!Z\!\!-\!\!R_{18} \\ | \\ X_1 \;\; X_2 \end{array}$$

or

In another embodiment of the invention, at least one of $R_1$, $R_2$, $R_3$ and $R_4$ is other than hydrogen.

In another embodiment of the invention, R is hydrogen, OH, $OC_{1-2}$ alkyl, $C_{1-2}$ alkyl, $C_{1-2}$ haloalkyl, $C_{2-3}$ alkenyl, $C_{2-3}$ alkynyl, aryl substituted by one or more groups $Y_1$, $CH_2$-aryl wherein the aryl group is substituted by one or more groups $Y_1$, $COC_{1-2}$ alkyl, $CONH_2$, NHCHO, $NH_2$, $NHSO_2C_{1-2}$ alkyl, or $NHCO_2C_{1-2}$ alkyl.

In another embodiment of the invention, R is hydrogen, OH, $OCH_3$, $OCF_3$, $COCH_3$, $OCOCH_3$, $CONH_2$, NHCHO, $NH_2$, $NHSO_2CH_3$, or $NHCO_2CH_3$.

In another embodiment of the invention, R is hydrogen, OH, $OCH_3$, or $OCF_3$.

In another embodiment of the invention, $Y_3$ is hydrogen.

In another embodiment of the invention, $R_1$, $R_2$, $R_3$ and $R_4$ are each, independently, one of the following structures:

[chemical structures]

or $R_1$ and $R_2$, $R_2$ and $R_3$ and/or $R_3$ and $R_4$ are bonded together to 5 to 7 membered alkyl group or a bridged heterocyclic ring.

In another embodiment of the invention, $R_1$, $R_2$, $R_3$ and $R_4$ are each, independently, hydrogen, methyl or ethyl.

In another embodiment of the invention, $R_1$, $R_2$, $R_3$ and $R_4$ are each, independently, hydrogen or methyl.

In another embodiment of the invention, $R_1$, $R_2$, $R_3$ and $R_4$ are each, independently, hydrogen or methyl, wherein at least one of $R_1$, $R_2$, $R_3$ and $R_4$ is methyl.

In another embodiment of the invention, $R_5$ is hydrogen, $C_{1-4}$ alkyl or —$(CH_2)_n$-phenyl.

In another embodiment of the invention, $R_5$ is $$\begin{array}{c} R_{17} \\ | \\ R_{19}-\!\!-\!\!Z\!\!-\!\!R_{18} \\ | \\ X_1 \;\; X_2 \end{array}$$

In another embodiment of the invention:
R is hydrogen, OH, $OCH_3$, or $OCF_3$;
$Y_3$ is hydrogen;
$R_1$, $R_2$, $R_3$ and $R_4$ are each, independently, hydrogen, methyl or ethyl; and
$R_5$ is hydrogen, $C_{1-4}$ alkyl or —$(CH_2)_n$-phenyl.

In one preferred embodiment, $R_2$ is other than hydrogen as defined above. This substitution may increase opioid efficacy by an order of magnitude. The chiralty at the resulting stereocenter may be (R) or (S). Preferred substituents are $C_{1-8}$ alkyl, preferably methyl, ethyl and propyl.

In another embodiment of the invention at least one of $R_1$, $R_2$, $R_3$ and $R_4$ is other than hydrogen as defined above when $R_5$ is

[phenyl-$(Y_1)_o$ structure]

In another preferred embodiment of the present invention, the opioid receptor antagonists are as described in the following Examples section.

The present invention includes any and all combination of the different structural groups defined above, including those combinations not specifically set forth above.

As used throughout this disclosure, the terms "alkyl group" or "alkyl radical" encompass all structural isomers thereof, such as linear, branched and cyclic alkyl groups and moieties. Unless stated otherwise, all alkyl groups described herein may have 1 to 8 carbon atoms, inclusive of all specific values and subranges therebetween, such as 2, 3, 4, 5, 6, or 7 carbon atoms. Representative examples include methyl, ethyl, propyl and cyclohexyl.

As used throughout this disclosure, the terms "haloalkyl group" or "haloalkyl radical" encompass all structural isomers thereof, such as linear, branched and cyclic groups and moieties. Unless stated otherwise, all haloalkyl groups described herein may have 1 to 8 carbon atoms, inclusive of all specific values and subranges therebetween, such as 2, 3, 4, 5, 6, or 7 carbon atoms. A $C_{1-2}$ haloalkyl group is particularly preferred. At least one hydrogen atom is replaced by a halogen atom, i.e., fluorine, chlorine, bromine or iodine. In one embodiment, all of the hydrogen atoms are replaced with halogen atoms. Fluorine is preferred. Perfluoroalkyl groups are particularly preferred. Examples of haloalkyl groups include trifluoromethyl (—$CF_3$) and perfluoroethyl (—$CF_2CF_3$).

The alkenyl group or alkynyl group may have one or more double or triple bonds, respectively. As will be readily appreciated, when an alkenyl or alkynyl group is bonded to a heteroatom a double or triple bond is not formed with the carbon atom bonded directly to the heteroatom. Unless stated otherwise, all alkenyl and alkynyl groups described herein may have 2 to 8 carbon atoms, inclusive of all specific values and subranges therebetween, such as 3, 4, 5, 6, or 7 carbon atoms. Preferred examples include —CH=CH$_2$, —CH$_2$CH=CH$_2$, —CCH and —CH$_2$CCH.

The aryl group is a hydrocarbon aryl group, such as a phenyl, naphthyl, phenanthryl, anthracenyl group, which may have one or more C$_{1-4}$ alkyl group substituents.

The compounds of the present invention may be in the form of a pharmaceutically acceptable salt via protonation of the amines with a suitable acid. The acid may be an inorganic acid or an organic acid. Suitable acids include, for example, hydrochloric, hydroiodic, hydrobromic, sulfuric, phosphoric, citric, acetic, fumaric, tartaric, and formic acids.

The opioid receptor selectivity may be determined based on the binding affinities at the receptors indicated or their selectivity in opioid functional assays.

The compounds of the present invention may be used to bind opioid receptors. Such binding may be accomplished by contacting the receptor with an effective amount of the inventive compound. Of course, such contacting is preferably conducted in an aqueous medium, preferably at physiologically relevant ionic strength, pH, etc. Receptor antagonism is the preferred mode of action of the compounds described herein.

The inventive compounds may also be used to treat patients having disease states which are ameliorated by binding opioid receptors or in any treatment wherein temporary suppression of the kappa opioid receptor system is desired. Such diseases states include opiate addiction (such as heroin addiction), cocaine, nicotine, or ethanol addiction. The compounds of the present invention may also be used as cytostatic agents, as antimigraine agents, as immunomodulators, as immunosuppressives, as antiarthritic agents, as antiallergic agents, as virucides, to treat diarrhea, as antipsychotics, as antischizophrenics, as antidepressants, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds can be used in the treatment of Parkinson's disease as an adjunct to L-dopa for treatment of dyskinesia associated with the L-dopa treatment.

The compounds of the present invention are particularly useful for treating addiction, such as addiction to cocaine, alcohol, methamphetamine, nicotine, heroine, and other drugs of abuse. With respect to nicotine, the compounds of the present invention are also useful in treating nicotine withdrawal effects.

The compounds may be administered in an effective amount by any of the conventional techniques well-established in the medical field. For example, the compounds may be administered orally, intraveneously, or intramuscularly. When so administered, the inventive compounds may be combined with any of the well-known pharmaceutical carriers and additives that are customarily used in such pharmaceutical compositions. For a discussion of dosing forms, carriers, additives, pharmacodynamics, etc., see Kirk-Othmer Encyclopedia of Chemical Technology, Fourth Edition, Vol. 18, 1996, pp. 480-590, incorporated herein by reference. The patient is preferably a mammal, with human patients especially preferred. Effective amounts are readily determined by those of ordinary skill in the art. Studies by the present inventors show no toxicity and no lethality for the present compounds at amounts up to 300 mg/kg in mice.

The compounds of the present invention can be administered as a single dosage per day, or as multiple dosages per day. When administered as multiple dosages, the dosages can be equal doses or doses of varying amount, based upon the time between the doses (i.e. when there will be a longer time between doses, such as overnight while sleeping, the dose administered will be higher to allow the compound to be present in the bloodstream of the patient for the longer period of time at effective levels). Preferably, the compound and compositions containing the compound are administered as a single dose or from 2-4 equal doses per day.

Suitable compositions containing the present compounds further comprise a physiologically acceptable carrier, such as water or conventional pharmaceutical solid carriers, and if desired, one or more buffers and other excipients.

The compounds of the invention may be synthesized by, for example, the schemes shown in the following Examples. Those skilled in the art will appreciate that the synthesis of the exemplified compounds can readily be adapted for the preparation of other compounds within the scope of formula I.

EXAMPLES

Having generally described this invention, a further understanding can be obtained by reference to certain specific examples which are provided herein for purposes of illustration only and are not intended to be limiting unless otherwise specified.

Chemistry and Biology

Compounds 5a-f of the present invention may be synthesized, for example, in accordance with the reaction sequence shown in Scheme 1. The tert-butoxycarbonyl-protected starting piperazines 7a-e were prepared by treating the appropriate piperazine with Boc$_2$O or Boc-ON using standard conditions. The piperazines required for 7a-d were commercially available. Piperazine needed for 7e was synthesized according to reported methods.[1,2] The tert-butoxycarbonyl-protected piperazines 7a-e were coupled to 3-bromoanisole under palladium-catalyzed conditions to give 8a-e. Treatment of 8a-e with boron tribromide in methylene chloride at −78° C. effected removal of the tert-butoxycarbonyl group and demethylation of the methyl ether to give 9a-e. Reductive alkylation of 9a-e using 3-phenylpropionaldehyde and sodium triacetoxyborohydride in 1,2-dichloroethane yielded the desired 5a-e. Reductive alkylation of 9b using formaldehyde and Raney nickel under a hydrogen atmosphere yielded 5f.

Compounds 5g,h can be synthesized by the routes shown in Scheme 2. Compound 10 was coupled to 3-bromoanisole under palladium-catalyzed conditions to give 11. Subjection of 11 to palladium on carbon in refluxing aqueous acetic acid removed the N-allyl-protecting group to give 12. Treatment of 12 with boron tribromide in methylene chloride at −78° C. affected demethylation of 12 to give the phenol 13. Reductive alkylation of 13 using 3-phenylpropionaldehyde and sodium triacetoxyborohydride in 1,2-dichloroethane yielded 6h. Treatment of 10 with (Boc$_2$)O in methylene chloride containing triethylamine gives the N-allyl, N-Boc-protected piperazine 14. Subjection of 14 to palladium on carbon in refluxing aqueous acetic acid selectively removed the N-allyl group to give 15. Compound 15 was coupled to 3-bromoanisole under palladium-catalyzed conditions to yield 16. Treatment of 16 with boron tribromide in methylene chloride at −78° C. effected removal of the tert-butoxycarbonyl group and demethylation of the methyl ether to give 17. Reductive alkylation of 17 using 3-phenylpropanaldehyde and sodium triacetoxyborohydride in 1,2-dichloroethane afforded the desired 5g.

Scheme 3 outlines the synthesis of 5i and 5j. Compound 9b is coupled with N-Boc-valine using BOP to give an amide which is not isolated but reduced directly to 5i using diborane in tetrahydrofuran. Coupling of 5i with 7-OH-Boc-D-Tic using BOP in tetrahydrofuran followed by treatment with trifluoroacetic acid in methylene chloride yielded 5j.

Biology

Measures of opioid receptor antagonism and specificity were obtained by monitoring the ability of selected test compounds to inhibit stimulation of [$^{35}$S]GTPγS binding produced by the selective agonists (D-Ala$^2$,MePhe$^4$,Gly-ol$^5$)enkephalin (DAMGO, mu receptor) cyclo[D-Pen$^2$,D-Pen$^5$] enkephalin (DPDPE, delta) and 5,7,8-(−)-N-methyl-N-[7-(1-pyrrolidinyl)-1-oxaspiro[4,5]dec-8-yl]benzeneacetamide (U69,593, kappa) in cloned human receptors (Table 1).

Results

Compounds 5a-j show high efficacy (low $K_e$ values) for the kappa opioid receptor in the [$^{35}$S]GTPγS in vivo functional assay, particularly 5b-e, 5g, and 5j. The compounds of the present invention are potent kappa opioid receptor antagonists in an in vitro functional test. Some compounds showed good selectivity for the kappa relative to the mu and delta opioid receptors.

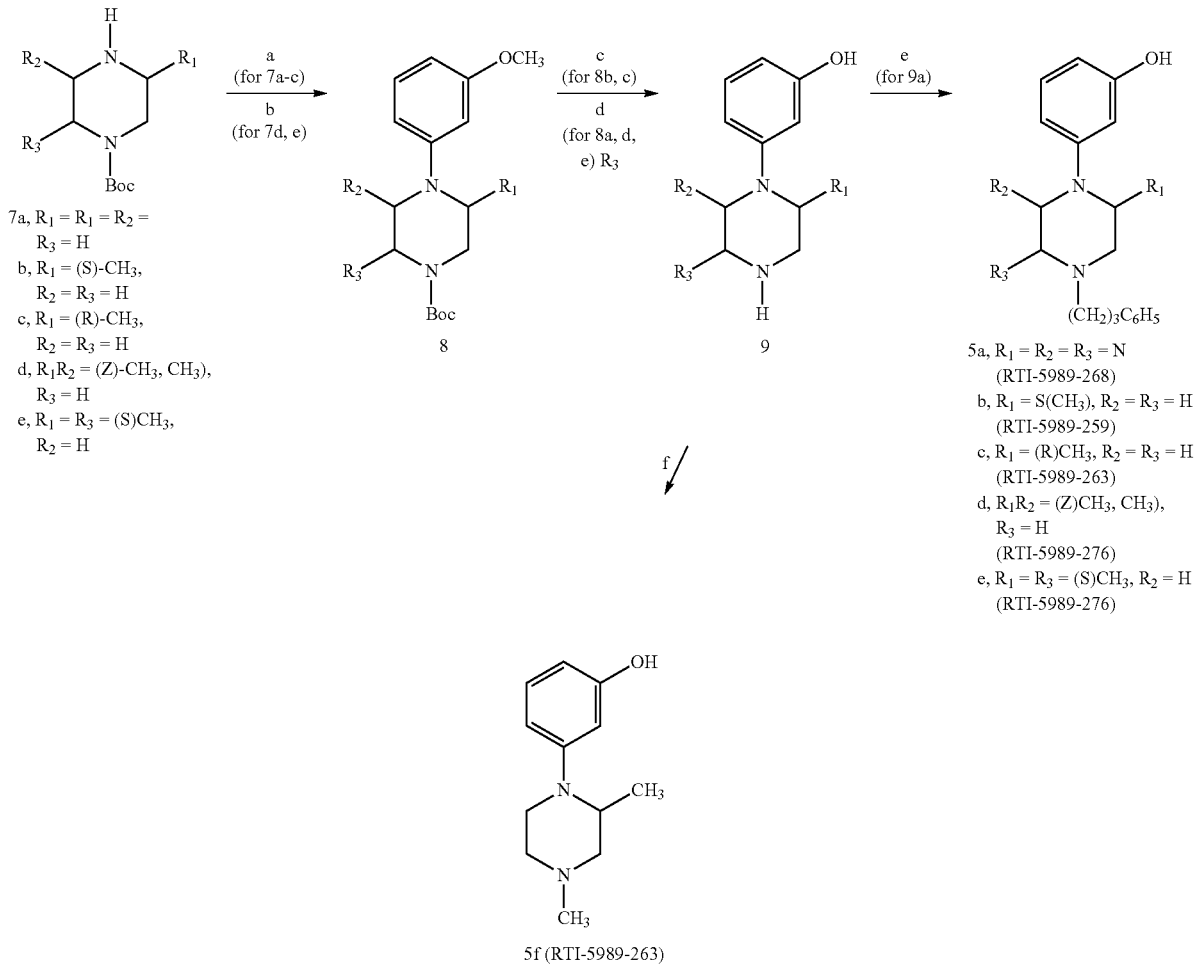

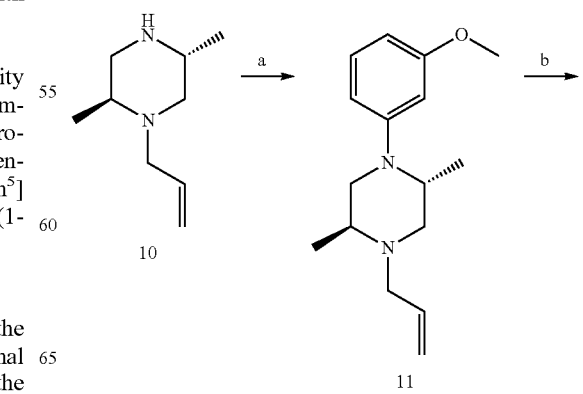

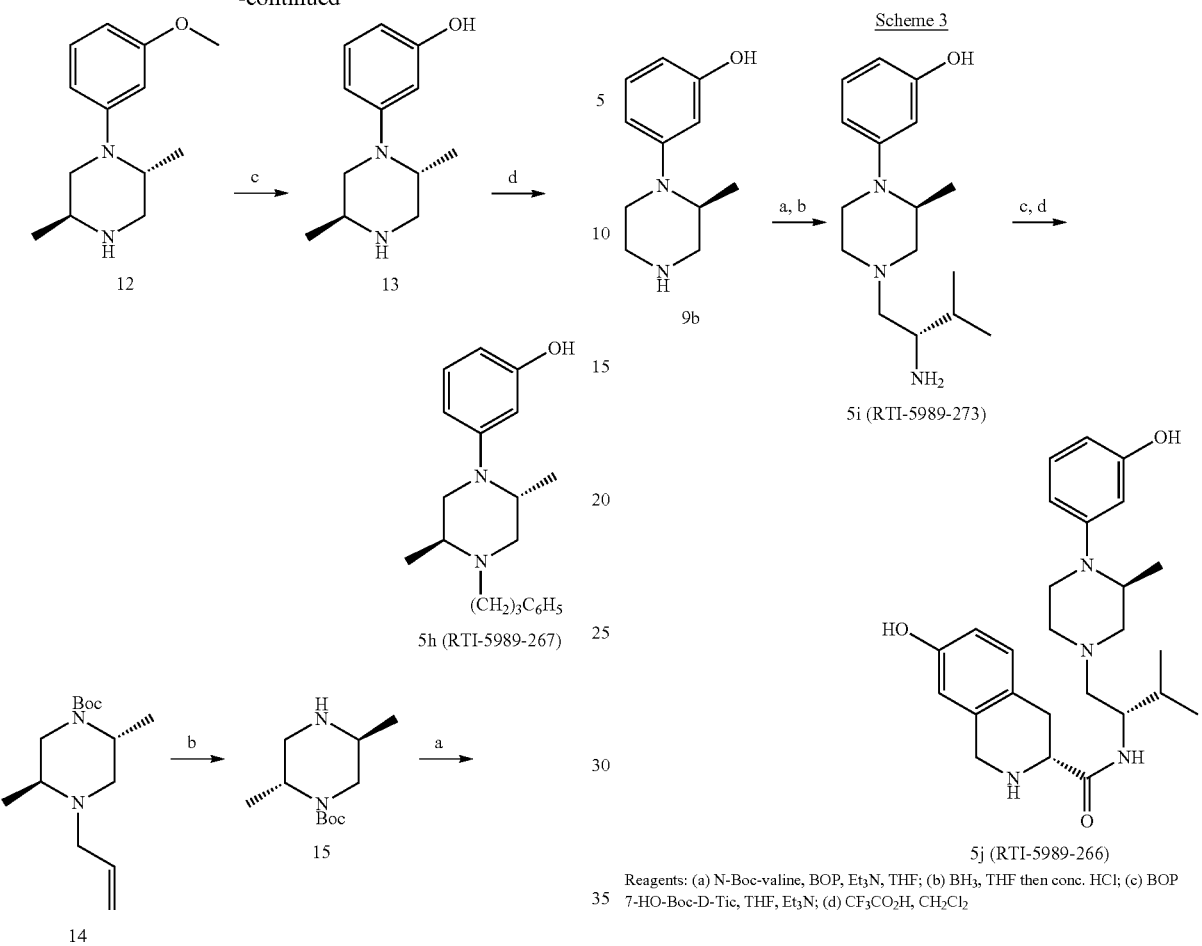
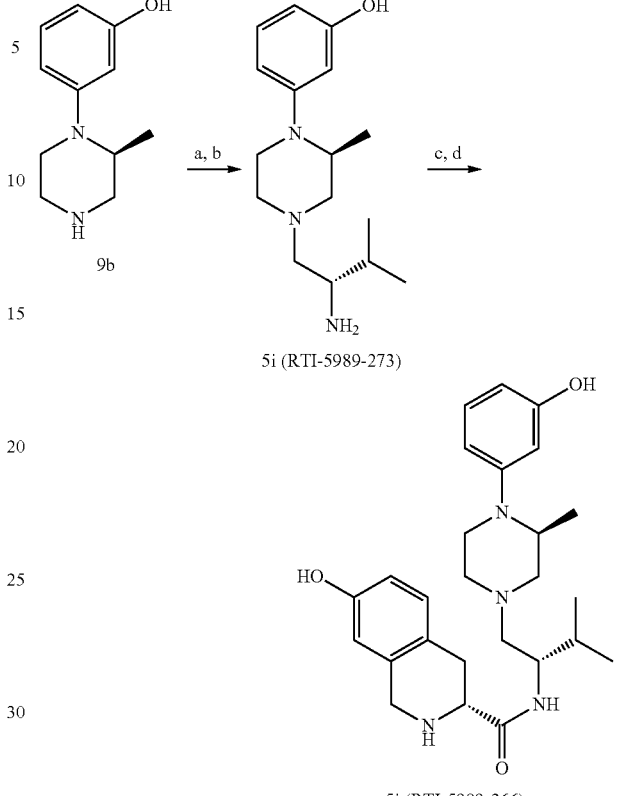

Reagents: (a) 3-bromoanisole, Pd$_2$(dba)$_3$, KOtBu, P(OtBu)$_3$, toluene, 110° C., sealed vessel; (b) Pd/C, CH$_3$CO$_2$H, H$_2$O, reflux; (c) BBr$_3$, CH$_2$Cl$_2$, -78° C.; (d) C$_6$H$_5$(CH$_2$)$_3$CHO, NA(OAc)$_3$BH, ET$_3$N, DCE.

Reagents: (a) N-Boc-valine, BOP, Et$_3$N, THF; (b) BH$_3$, THF then conc. HCl; (c) BOP 7-HO-Boc-D-Tic, THF, Et$_3$N; (d) CF$_3$CO$_2$H, CH$_2$Cl$_2$ Experimental General Procedures for the Preparation of 3-[4-(Substituted piperazin-1-yl)]phenols (6a-e)

a. Palladium-Catalyzed 3-Methoxyphenylation Procedure.

In a thick-walled glass sealable tube, 1 eq of piperazine 7a-c was dissolved in 20 mL of dry toluene along with 1.5 eq of 3-bromoanisole, 0.005 eq of Pd$_2$(dba)$_3$, 1.5 eq of KOtBu, and 0.01 eq of P(tBu)$_3$ as a 1M solution in toluene. The tube was flushed with argon, sealed, and heated to 110° C. for 16 h. The vessel was cooled to room temperature, opened, and the contents filtered through celite. The filtered solution was reduced to a fifth of its volume by evaporation under reduced pressure. The remaining solution was subjected to column chromatography on silica gel eluting with hexanes-EtOAc (5:1). The combined fractions containing the product were subjected to rotary evaporation, and the remaining oil was dried under high vacuum.

b. Transition Metal-Free 3-Methoxyphenylation.[3]

In a round-bottom flask equipped with a condenser under an argon dry atmosphere, 1.1 eq of KN(Si(CH$_3$)$_3$)$_2$ was suspended in 7 mL of dry 1,4-dioxane. The piperazines 7d,e, 1 eq, was added followed by 1 eq of 3-bromoanisole. The reaction mixture was stirred at 100° C. for 2.5 h, cooled to room temperature, and quenched with H$_2$O (10 mL). To the mixture was added Et$_2$O (15 mL) and shaken vigorously. The layers were separated, and the aqueous layer was extracted twice with Et$_2$O (10 mL). The pooled organic solution was concentrated by rotary evaporation, and the residue was subjected to column chromatography on silica gel eluting with hexane-EtOAc (5:1). The combined fractions containing the product were subjected to rotary evaporation, and the remaining oil was dried under high vacuum.

c. Removal of the N-Boc and O-Me Protecting Groups with $BBr_3$.

Under an argon atmosphere, 1 eq of Boc-protected phenylpiperazine 8 was dissolved in $CH_2Cl_2$ (20 mL), and the solution was cooled to −78° C. Into this mixture, 4 eq of $BBr_3$ as a 1 M solution in $CH_2Cl_2$ were introduced. The reaction mixture was stirred for 4 h, warmed to 0° C., and stirred for an additional 2 h. Into this solution dry MeOH (20 mL) was slowly added, and the solution was stirred for 5 min. The solvents were then removed under reduced pressure at 25° C. The residue was redissolved in MeOH (20 mL), and the solvents were removed again under reduced pressure to afford a residue that was recrystallized or converted to the freebase and purified by column chromatography on silica gel to yield the product.

d. Removal of the N-Boc and O-Me Protecting Groups with Conc. HBr.

In a round-bottom flask 8 were dissolved in conc. HBr, and the solution was refluxed for 16 h. Removal of the solvents by rotary evaporation gave a residue that was dissolved in MeOH. This solution was stirred over excess $NaHCO_3$ for 10 min and then filtered. The solution was concentrated under reduced pressure and subjected to column chromatography on silica gel to afford the product.

e. Reductive Alkylation of 9a-e with 3-Phenylpropanaldehyde.

In a dry flask 1 eq of phenylpiperazine 9a-e was dissolved in 1,2-dichloroethane (20 mL) along with 1.5 eq of 3-phenylpropanaldehyde and 1.5 eq of $Et_3N$. The solution was cooled to 0° C., and 1.5 eq of $Na(OAc)_3BH$ was then added. The reaction mixture was stirred for 1 h at 0° C., allowed to warm to 25° C. After stirring for 2 h, the reaction mixture was added to a concentrated solution of $NaHCO_3$ (20 mL) and shaken vigorously. The layers were separated, and the organic layer was washed once with $H_2O$ (5 mL) and once with brine (5 mL). The organic solution was dried ($MgSO_4$), filtered, and the solvents removed under reduced pressure to yield the product which was purified as specified.

1-tort-Butoxycarbonyl-4-(3-methoxyphenyl)piperazine (8a)

General procedure a. was employed using 0.996 g (5.35 mmol) of commercially available Boc-piperazine 7a to obtain, after chromatography, 1.53 g (98%) of 8a as a yellowish solid: mp 62-63° C. $^1$H NMR ($CDCl_3$) δ 7.18 (t, 1H), 6.54 (m, 1H), 6.46. (s, 1H), 6.45 (m, 1H), 3.79 (s, 3H), 3.57 (m, 4H), 3.13 (m, 4H), 1.48 (s, 9H). ESIMS: m/z 293 (M+H$^+$, 100).

(S)-tert-Butyl-4-(3-methoxyphenyl)-3-methylpiperazine-1-carboxylate (8b)

General procedure a. was employed using 1.32 g (6.60 mmol) of Boc-piperazine 7b[4] to obtain, after chromatography, 1.19 g (59%) of 8b as a yellow oil with spectra identical to that of 8c.

(R)-tert-Butyl-4-(3-methoxyphenyl)-3-methylpiperazine-1-carboxylate (8c)

General procedure a. was employed using 1.00 g (5.00 mmol) of Boc-piperazine 7b[4] to obtain, after chromatography, 841 mg (55%) of 8c as a yellow oil. $^1$H NMR ($CDCl_3$) δ 7.17 (t, 1H), 6.67 (d, 1H), 6.43. (d, 1H), 4.37 (bm, 1H), 3.84, (m, 1H), 3.79 (s, 3H), 3.77 (bd, 1H), 3.33 (m, 1H), 3.18 (bm, 2H), 1.48 (s, 9H), 1.01 (d, 3H). ESIMS: m/z 425 (M+Na$^+$, 100).

(Z)-1-tert-Butoxycarbonyl-4-(3-methoxyphenyl)-3,5-dimethylpiperazine (8d)

General procedure b. was employed using 588 mg (2.74 mmol) of Boc-piperazine 7d to obtain, after chromatography, 407 mg (46%) of 8d as a yellow oil. $^1$H NMR ($CDCl_3$) δ 7.20 (t, 1H), 6.69 (m, 3H), 4.15 (m, 0.7H), 3.89 (bm, 1.3H), 3.79 (s, 3H), 3.06 (m, 2H), 2.88 (m, 2H), 1.48 (d, 9H), 1.20 (d, 2.1H), 0.81 (d, 3.1H). ESIMS: m/z 321 (M+H$^+$, 50).

(2S,5S)-1-tert-Butoxycarbonyl-4-(3-methoxyphenyl)-2,5-dimethylpiperazine (8e)

General procedure b. was employed using 433 mg (2.02 mmol) of Boc-piperazine 7e to obtain, after chromatography, 397 mg (65%) of 8e as a yellow oil. $^1$H NMR ($CDCl_3$) δ 7.17 (t, 1H), 6.52 (d, 1H), 6.47-6.45 (m, 1H), 4.15 (q, 1H), 4.03-3.98 (m, 1H), 3.41 (q, 1H), 3.30 (dd, 1H), 2.97-2.90 (dd, 1H), 2.84 (dd, 1H), 1.45 (s, 9H), 1.32 (d, 3H), 1.04 (d, 3H). ESIMS: m/z 321 (M+H$^+$, 50).

(2S,5R)-1-tert-Butoxycarbonyl-4-(3-methoxyphenyl)-2,5-dimethylpiperazine (16)

General procedure a. was employed using 1.04 g (3.79 mmol) of Boc-piperazine 15 to obtain, after chromatography, 288 mg (24%) of 16 as a yellow oil. $^1$H NMR ($CDCl_3$) δ 7.12 (t, 1H), 6.46 (d, 1H), 6.37 (s, 1H), 6.35 (d, 1H), 4.39 (b, 1H), 3.94 (bm, 1H), 3.79 (s, 3H), 3.78 (m, 1H), 3.40 (dd, 1H), 3.25 (dd, 1H), 3.11 (d, 1H), 1.48 (s, 9H), 1.25 (d, 3H), 1.03 (d, 3H). ESIMS: m/z 221 (M-Boc+H$^+$, 95;), 321 (M+H$^+$, 20).

(2R,5S)-1-Allyl-4-(3-methoxyphenyl)-2,5-dimethylpiperazine (11)

General procedure a. was employed using 1.00 g (6.48 mmol) of allyl-piperazine 10[5] to obtain, after chromatography, 715 mg (55% yield) of 11 as a yellow oil. $^1$H NMR ($CDCl_3$) δ 7.19 (t, 1H), 6.67 (dd, 1H), 6.62 (m, 1H), 6.56 (dd, 1H), 5.91 (m, 1H), 5.27-5.17 (m, 2H), 3.79 (s, 3H), 3.45-3.26 (m, 2H), 3.13 (dd, 1H), 3.00-2.89 (m, 2H), 2.82-2.64 (m, 2H), 2.21 (dd, 1H), 1.06 (d, 3H), 0.98 (d, 3H). ESIMS: m/z 261 (M+H$^+$, 100).

3-piperazine-phenol Dihydrobromide (9a)

General procedure d. was employed using 1.39 of 8a and 20 mL of conc. HBr. Recrystallization from MeOH gave 1.05 (65%) of 9a as pink crystals: mp>220° C. $^1$H NMR ($d_6$-DMSO) δ 8.75 (bs, 2H), 7.29 (bs, 2H), 7.16 (t, 1H), 6.55 (d, 1H), 6.51 (s, 1H), 5.45 (d, 1H), 3.36 (m, 2H), 3.22 (m, 4H), 2.50 (m, 2H). ESIMS: m/z 179 (M+H$^+$, 100).

(S)-3-(2-Methylpiperazin-1-yl)phenol (9b) Dihydrobromide

General procedure c. was employed using 714 mg (2.44 mmol) of 8b affording a tan solid that was triturated under cold MeOH and collected by filtration, 624 mg (76%): mp>220° C. This compound had identical spectral information as 9c (see below).

(R)-3-(2-Methylpiperazin-1-yl)phenol (9c) Dihydrobromide

General procedure c. was employed using 780 mg (2.54 mmol) of 8c affording a tan solid that was triturated under cold MeOH and collected by filtration, 685 mg (76%): mp>220° C. $^1$H NMR (CD$_3$OD) δ 7.33 (q, 1H, ArH), 6.97 (d, 1H, ArH), 6.94 (s, 1H, ArH), 6.80 (d, 1H, ArH), 4.15 (m, 1H, NCH), 3.76 (m, 1H, NCH), 3.71 (bd, 2H, NCH), 3.49 (dd, 1H, NCH), 1.18 (d, 3H, CH$_3$). ESIMS: m/z 193 (M+H$^+$, 100).

(Z)-3-(2,6-Dimethylpiperazin-1-yl)phenol (9d)

General procedure d. was employed using 407 mg (1.27 mmol) of 8d and 10 mL of conc. HBr. The dihydrobromide salt was dissolved in MeOH, stirred over 200 mg of NaHCO$_3$ for 10 min, and filtered. The solution was concentrated under reduced pressure and subjected to column chromatography on silica gel eluting with CMA80 to afford 180 mg (65%) of 9d as a brown solid: mp>220° C. $^1$H NMR (CDCl$_3$) δ 7.15 (t, 1H), 6.68 (m, 2H), 3.14 (m, 4H), 2.71 (dd, 2H, J=12 Hz), 0.80 (d, 3H). ESIMS: m/z 207 (M+H$^+$, 100).

(2S,5S)-3-(2,5-Dimethylpiperazin-1-yl)phenol (9e)

General procedure d. was employed using 397 mg (1.80 mmol) of 8e and 10 mL of conc. HBr. The dihydrobromide salt was dissolved in MeOH, stirred over 200 mg of NaHCO$_3$ for 10 min and then filtered. The solution was concentrated under reduced pressure and subjected to silica-gel column chromatography eluting with CMA80-CH$_2$Cl$_2$ (1:1) to afford 522 mg (29%) of 9e as a grey solid: mp>220° C. $^1$H NMR (CDCl$_3$) δ 7.10 (q, 1H), 6.52 (m, 1H), 6.45 (s, 1H), 6.41 (m, 1H), 4.23 (m, 2H), 3.89-3.39 (m, 4H), 3.03 (dd, 2H), 1.45 (d, 3H), 1.15 (d, 3H). ESIMS: m/z 207 (M+H$^+$, 100).

3-[(2S,5R)-2,5-Dimethylpiperazin-1-yl]phenol (17) Dihydrobromide

General procedure c. was employed using 288 mg (0.90 mmol) of 16 affording a crimson-colored residue that was pure by NMR (100%). $^1$H NMR (CD$_3$OD) δ 7.44 (t, 1H), 7.23 (m, 2H), 6.97 (m, 1H), 4.39 (m, 1H), 4.22 (m, 1H), 3.97-3.82 (m, 2H), 3.71 (m, 1H), 3.29 (m, 1H), 1.48 (d, 3H), 1.25 (d, 3H). ESIMS: m/z 207 (M+H$^+$, 100).

3-[(2R,5S)-2,5-Dimethylpiperazin-1-yl]phenol (13)

In a round-bottom flask, 715 mg (2.74 mmol) of 12 was dissolved in 10 mL CH$_3$COOH and 5 mL of H$_2$O. To this mixture was added 50 mg of 10% Pd on carbon, and the suspension was heated and stirred at reflux for 12 h. The mixture was cooled, filtered, and the solvents evaporated under reduced pressure. To the residue was added 20 mL of conc. NaHCO$_3$, and this mixture was extracted thoroughly with EtOAc. The pooled organic extracts were washed once with brine, dried over MgSO$_4$, and the solvents removed under reduced pressure to yield 605 mg of an orange oil that was pure (2R,5S)-1-(3-methoxyphenyl)-2,5-dimethylpiperazinium acetate by NMR. $^1$H NMR (CDCl$_3$) δ 7.21 (t, 1H), 6.73 (dd, 1H), 6.62 (m, 1H), 6.67 (m, 1H), 6.63 (m, 1H), 3.79 (s, 3H), 3.12-2.90 (m, 4H), 2.70 (dd, 1H), 2.46 (dd, 1H), 1.07 (d, 3H), 0.93 (d, 3H). ESIMS: m/z 221 (M+H$^+$, 100). General procedure c. was employed using 363 mg (1.65 mmol) of this oil affording a residue that was dissolved in 5 mL of MeOH and stirred over excess NaHCO$_3$. The mixture was filtered, and the solvents subjected to rotary evaporation to afford a residue that was purified by chromatography affording 215 mg of 13 as a white solid (63% yield). Spectral information for this compound was found to be identical to 17.

3-(4-Phenylpropylpiperazin-1-yl)phenol (5a) Dihydrochloride

General procedure e. was employed with 250 mg (0.735 mmol) of 9a. The crude product was subjected to flash-column chromatography on silica gel eluting with CMA80-CH$_2$Cl$_2$ (1:1). The freebase thus recovered was converted to the dihydrochloride salt by dissolving in 2 mL of a 2 M HCl solution in EtOH and removing the solvents under reduced pressure. The solids were suspended in EtOAc and collected by filtration to yield 55 mg (20%) of 5a.2HCl as a tan powder: mp 194-201° C. (dec). $^1$H NMR (CD$_3$OD) δ 7.33-7.21 (m, 5H), 7.09 (t, 1H), 6.52-6.38 (m, 3H), 3.81-3.76 (bd, 2H), 3.67-3.63 (bd, 2H), 3.29-3.18 (m, 4H), 3.09-3.00 (bt, 2H), 2.75 (t, 2H), 2.13 (m, 2H). ESIMS: m/z 297 (M+H$^+$, 100). Anal. calcd for C$_{19}$H$_{26}$Cl$_2$N$_2$O: C, 61.79; H, 7.10; N, 7.55. Found: C, 61.72; H, 7.10; N, 7.38.

(S)-3-(2-Methyl-4-phenylpropylpiperazin-1-yl)phenol (5b) Dihydrochloride

General procedure e. was employed using 247 mg (0.886 mmol) of 9b. The dihydrochloride salt was made by dissolving the crude product in 5 mL of a 2 M solution of HCl in EtOH and removing the solvents under reduced pressure. This salt was recrystallized from EtOH-EtOAc to yield 126 mg (37%) of 5b.2HCl as a white powder: mp>220° C. [α]=+2.17 (c 0.46, CH$_3$OH). The spectral information gathered for this compound were identical as those obtained for 5c (see below). Anal. calcd for C$_{20}$H$_{28}$Cl$_2$N$_2$O: C, 62.66; H, 7.36; N, 7.31. Found: C, 62.45; H, 7.53; N, 7.29.

(R)-3-(2-Methyl-4-phenylpropylpiperazin-1-yl)phenol (5c) Dihydrochloride

General procedure e. was employed using 175 mg (0.886 mmol) of 9c. The dihydrochloride salt was made by dissolving the product in 5 mL of a 2 M solution of HCl in EtOH and removing the solvents under reduced pressure. This salt was recrystallized from EtOH-EtOAc to yield 55 mg (19%) of 5c.HCl as a white powder: mp>220° C.; [α]–2.17 (c 0.46, CH$_3$OH). $^1$H NMR (CD$_3$OD) δ 7.40-7.27 (m, 9H), 3.95-3.70 (b, 2H), 3.70-3.50 (b, 2H), 3.33 (m, 2H), 3.30 (m, 3H), 2.78 (t, 2H), 1.17 (d, 3H). ESIMS: m/z 311 (M+H$^+$, 100). Anal. calcd for C$_{20}$H$_{28}$Cl$_2$N$_2$O: C, 62.66; H, 7.36; N, 7.31. Found: C, 62.15; H, 7.36; N, 7.02.

(Z)-3-(2,6-Dimethyl-4-(3-phenylpropyl)piperazin-1-yl)phenol (5d) Dihydrochloride General procedure e. was employed using 65 mg (0.315 mmol) of 9d. The crude product was subjected to preparative TLC eluting with CMA80-CH$_2$Cl$_2$ (1:1) which afforded 20 mg (20%) of 5d as an amber-colored residue. The 5d.2HCl was prepared by dissolving this material in 5 mL of 2 M HCl in EtOH and removing the solvents under reduced pressure: mp 210-212° C. $^1$H NMR (freebase in CDCl$_3$) δ 7.30-7.18 (m, 4H), 7.13 (t, 1H), 6.67 (d, 1H), 6.66 (s, 1H), 6.59 (dd, 1H), 3.19 (m, 2H), 2.81 (dd, 2H), 2.66 (t, 2H, J=9 Hz), 2.41 (dd, 2H), 2.08 (dd, 2H, J=9 Hz), 1.88 (m, 3H), 0.81 (d, 6H, J=6 Hz). ESIMS: m/z 325 (M+H$^+$, 100). Anal. calcd for C$_{21}$H$_{30}$Cl$_2$N$_2$O.H$_2$O: C, 60.72; H, 7.76; N, 6.74. Found: C, 61.10; H, 7.80; N, 6.63.

3-[(2S,5S)-2,5-Dimethyl-4-(3-phenylpropyl)piperazin-1-yl]phenol (5e) Dihydrochloride General procedure e. was employed using 83 mg (0.225 mmol) of 9e. The crude product was subjected flash column chromatography on silica gel eluting with CMA80-CH$_2$Cl$_2$ (1:1) which afforded an amber-colored residue. The dihydrochloride was prepared by dissolving this residue in 5 mL of 2 M HCl in EtOH and removing the solvents under reduced pressure. The residue was dissolved in 1 mL of MeOH, and the white crystals of 5e.2HCl were collected by filtration to afford 8 mg (9%): mp>220° C. (dec). $^1$H NMR (freebase in CDCl$_3$) δ 7.30-7.18 (m, 4H), 7.13 (t, 1H), 6.67 (d, 1H), 6.66 (s, 1H), 6.59 (dd, 1H), 3.19 (m, 2H), 2.81 (dd, 2H), 2.66 (t, 2H, J=9 Hz), 2.41 (dd, 2H), 2.08 (dd, 2H, J=9 Hz), 1.88 (m, 3H), 0.81 (d, 6H, J=6 Hz). ESIMS: m/z 325 (M+H$^+$, 100). Anal. calcd for C$_{21}$H$_{30}$Cl$_2$N$_2$O: C, 60.72; H, 7.76; N, 6.74. Found: C, 61.01; H, 7.70; N, 6.80.

(S)-3-(2,4-Dimethylpiperazin-1-yl)phenol (5f) Dihydrochloride

At room temperature and under an atmosphere of H$_2$ were stirred 109 mg (0.567 mmol) of the piperazine 9b, 0.5 mL of Raney nickel slurry, and formaldehyde (0.5 mL of 37% in H$_2$O) in EtOH for 8 h in 15 mL of EtOH. The suspension was filtered and the solvents evaporated to yield a crude residue that was separated by silica gel column chromatography eluting with CMA80-CH$_2$Cl$_2$ (1:1). The fractions containing the product were removed of solvent by rotary evaporation, acidified with a 2 M HCl solution in EtOH, and crystallized by addition of Et$_2$O and cooling to give 5f.2HCl: mp 179-183° C.; [α]$_D$+4.4° (c 0.18, MeOH). $^1$H NMR (freebase in CDCl$_3$) δ 7.09 (t, 1H), 6.50 (dd, 1H), 6.41 (t, 1H), 6.34 (dd, 1H), 3.75 (m, 1H), 3.15 (m, 1H), 2.76 (m, 1H), 2.55 (m, 2H), 2.36 (m, 1H), 2.32 (s, 3H), 1.06 (d, 3H). ESIMS: m/z 207 (M+1, 100). Anal. calcd for C$_{12}$H$_{20}$Cl$_2$N$_2$O: C, 51.62; H, 7.22; N, 10.03. Found: C, 51.88; H, 7.51; N, 9.89.

3-((2S,5R)-2,5-Dimethyl-4-(3-phenylpropyl)piperazin-1-yl)phenol (5g) Dihydrochloride General procedure e. was employed using 175 mg (0.475 mmol) of 17. The dihydrochloride salt was made by dissolving the crude product in 5 mL of a 2 M solution of HCl in EtOH, and removing the solvents under reduced pressure. The salt was triturated under EtOH-iPrOH, collected by filtration, and dried under vacuum to afford 88 mg (47%) of pure 5g.HCl as a white powder: mp 199° C. (dec); [α]$^{25}_D$- 9.47 (c 0.57, MeOH). $^1$H NMR (CD$_3$OD) δ 7.35-7.22 (m, 6H), 7.00-6.75 (m, 3H), 4.00-3.78 (m, 3H), 3.65-3.29 (m, 4H), 3.20 (dt, 1H), 2.80 (m, 2H), 2.15 (m, 1H), 1.38 (d, 3H), 1.11 (d, 3H). ESIMS: m/z 325 (M+H$^+$, 100). Anal. calcd for C$_{21}$H$_{30}$Cl$_2$N$_2$O: C, 63.47; H, 7.61; N, 7.05. Found: C, 63.47; H, 7.67; N, 6.89.

3-((2R,5S)-2,5-Dimethyl-4-(3-phenylpropyl)piperazin-1-yl)phenol (5h) Dihydrochloride General procedure e. was employed using 47 mg (0.228 mmol) of 13. The dihydrochloride salt was made by dissolving the crude product in 5 mL of a 2 M solution of HCl in EtOH, and removing the solvents under reduced pressure. The crude salt was triturated under EtOH-iPrOH, collected by filtration and dried under vacuum to afford 14 mg (15%) of pure 5h.2HCl as a white powder with identical melting point (199° C. dec) and spectra as those reported for 5g.2HCl: [α]$^{25}_D$+9.5 (c 0.55, MeOH). Anal. calcd for C$_{21}$H$_{30}$Cl$_2$N$_2$O: C, 63.47; H, 7.61; N, 7.05. Found: C, 63.31; H, 7.51; N, 7.29.

3-{(2S)-4-[(2S)-2-Amino-3-methylbutyl]-2-methylpiperazin-1-yl}phenol (5i) Trihydrochloride In a round-bottom flask, 570 mg (2.49 mmol) of 9b were dissolved in dry THF (30 mL) along with 542 mg (2.49 mmol) of N-Boc-L-valine. The solution was cooled to 0° C. in an ice-bath and 1.38 mL (9.97 mmol) of Et$_3$N were added followed by 1.10 g (2.49 mmol) of BOP. The flask was removed from the ice bath and the reaction was stirred for 2 h. The solution was then dumped on concentrated aqueous NaHCO$_3$ solution, and the mixture extracted three times with 15 mL of EtOAc. The pooled organic extracts were washed with brine, dried (MgSO$_4$), filtered, and the solution concentrated to leave a residue that was purified by flash column chromatography on silica gel to yield 415 mg (42%) of the intermediate amide. This amide was dissolved in 20 mL of THF, and 3.18 mL (3.18 mmol) of a 1 M solution of BH$_3$ THF were added. The solution was stirred at reflux overnight cooled to RT and quenched with 5 mL of H$_2$O. Into this solution was added 10 mL of conc. HCl, and the mixture was stirred for 1 hr and 20 mL of water were added. Solid NaHCO$_3$ was then added to adjust the solution to a pH of 8. The mixture was extracted three times with 5 mL of CH$_2$Cl$_2$, washed with brine, and dried (MgSO$_4$). Rotary evaporation of the solution afforded a residue that was purified by flash-column chromatography on silica gel eluting with CMA80-hexanes-EtOAc (6:2:1) to yield 241 mg (82%) of 5i as a white solid. An analytic sample of the trihydrochloride salt 5i.3HCl was prepared by recrystallization from EtOAc-hexanes: mp 210-212° C.; [α]$^{25}_D$+ 48.8° (c 0.1, MeOH). NMR (CD$_3$OD) δ 7.46-7.40 (t, 1H), 7.16 (m, 2H), 6.98 (d, 1H), 4.14 (m, 1H), 3.96 (m, 1H), 3.65 (m, 1H), 3.30 (m, 3H), 2.95 (m, 3H), 2.00 (m, 1H) 1.23-1.03 (m, 9H). ESIMS: m/z 278 (M+H$^+$, 100). Anal. calcd for C$_{16}$H$_{30}$Cl$_3$N$_3$O.H$_2$O: C, 47.47; C, 7.97; N, 10.38. Found: C, 47.02; H, 7.96; N, 10.03.

(3R)-7-Hydroxy-N-[(1S)-1-{[(3S)-4-(3-hydroxyphenyl)-3-methylpiperazin-1-yl]methyl}-2-methylpropyl]-1,2,3,4-tetrahydroisoquinoline-3-carboxamide (5j) Trihydrochloride In a round-bottom flask, 120 mg (0.432 mmol) of 5i and 133 mg (0.454 mmol) of 7-OH-Boc-D-Tic were dissolved in dry THF (15 mL), and the solution was cooled to 0° C. Into this solution 0.06 mL of Et$_3$N were added followed by 201 mg (0.454 mmol) of BOP. The solution was warmed up to room temperature, stirred for 3 h, and then added to an ice-cold concentrated NaHCO$_3$ solution. The mixture was extracted three times with 5 mL of EtOAc. The pooled organic extracts were washed once with conc. NaHCO$_3$ solution, once with brine, and dried (MgSO$_4$). The filtrates were concentrated under reduced pressure to yield a residue that was dissolved in 5 mL of CH$_2$Cl$_2$ and 3 mL of CF$_3$CO$_2$H and stirred overnight. The solvents were reduced under reduced pressure to yield a residue, which was stirred with 10 mL of conc. NaHCO$_3$ solution and 10 mL of EtOAc. The layers were separated, and the aqueous layer was extracted three times with 3 mL of EtOAc. The pooled organic extracts were washed once with brine, dried (MgSO$_4$), and filtered. The filtrates were concentrated under reduced pressure to yield a residue that was purified by flash-column chromatography on silica gel eluting with CMA80-EtOAc-hexanes (2:1:1) to yield a residue that was dissolved in 3 mL of a 2 M solution of HCl in EtOH. The solvent was removed under reduced pressure to leave a solid that was triturated under MeOH to give 61 mg (31%) of 5j.3HCl: mp>220° C. (dec); [α]+67.6 (c 0.21, CH$_3$OH). $^1$H NMR (CD$_3$OD) δ 8.75 (d, 1H), 7.38 (b, 1H), 7.10 (b+d, 3H), 6.92 (b, 1H), 6.76 (dd, 1H), 6.67 (d, 1H), 4.44-4.33 (m, 6H), 3.91-3.67 (m, 3H), 3.67-3.50 (m, 2H), 3.50-3.35 (m, 2H), 3.31-3.21 (m, 1H), 2.81 (dd, 1H) 1.92 (m, 1H), 1.18 (b, 3H), 1.05 (t, 6H). ESIMS: m/z 453 (M+H$^+$, 100). Anal. calcd for C$_{26}$H$_{39}$Cl$_3$N$_4$O$_3$.3H$_2$O: C, 50.69; H, 7.36; N, 9.09. Found: C, 50.66; H, 7.09; H, 8.95.

TABLE 1

Comparison of Inhibition of Agonist Stimulated [$^{35}$S]GTPγS Binding in Cloned Human μ, δ, and κ-Opioid Receptors for Compounds

| compd | Structure | $R_1$ | $R_2$ | $R_3$ | $R_4$ | $R_5$ | μ, DAMGO $K_e$ (nM) | δ, DPDPE $K_e$ (nM) | κ, U69,593 $K_e$ (nM) | μ/κ | δ/κ |
|---|---|---|---|---|---|---|---|---|---|---|---|
| norBNI | | | | | | | 26 ± 7 | 29 ± 8 | 0.05 ± 0.02 | 520 | 580 |
| JDTic | A | | | | | a | 25.1 ± 3.5 | 76.4 ± 2.7 | 0.02 ± 0.01 | 1255 | 3830 |
| 2b | A | | | | | $CH_3$ | 29 ± 3 | 680 ± 240 | 155 ± 24 | | |
| 2c | A | | | | | $C_6H_5(CH_2)_3$ | 0.10 ± 0.02 | 0.90 ± 0.3 | 0.88 ± 0.20 | | |
| 5a | B | H | H | H | H | $C_6H_5(CH_2)_3$ | 8.5 ± 1.4 | 34 ± 6 | 15 ± 3 | | |
| 5b | B | H | (S)$CH_3$ | H | H | $C_6H_5(CH_2)_3$ | 0.88 ± 0.03 | 13.4 ± 4.2 | 4.09 ± 0.79 | | |
| 5c | B | H | (R)$CH_3$ | H | H | $C_6H_5(CH_2)_3$ | 1.0 ± 0.2 | 7.0 ± 2 | 1.5 ± 0.4 | | |
| 5d | B | (Z)$CH_3$, $CH_3$ | H | H | | $C_6H_5(CH_2)_3$ | 3 | 4300 | 3 | | |
| 5e | B | H | (S)$CH_3$ | H | (S)$CH_3$ | $C_6H_5(CH_2)_3$ | — | | 7 ± 0.3 | | |
| 5f | B | H | (S)$CH_3$ | H | H | $CH_3$ | 508 ± 26 | NA | 193 ± 19 | | |
| 5g | B | H | (S)$CH_3$ | H | (R)$CH_3$ | $C_6H_5(CH_2)_3$ | 6.1 ± 1.7 | 55 ± 3 | 4.2 ± 0.8 | | |
| 5h | B | H | (R)$CH_3$ | H | (S)$CH_3$ | $C_6H_5(CH_2)_3$ | 18 ± 4 | 179 ± 68 | 26 ± 7 | | |
| 5i | B | H | (S)$CH_3$ | H | H | $CH_2CH[(CH_3)_2CH]NH_2$ | 2 | 55 | 10 | | |
| 5j | B | H | (S)$CH_3$ | H | H | a | 22 ± 4 | 274 ± 48 | 2.7 ± 0.1 | | |

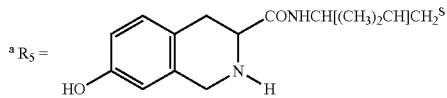

$^a R_5 = $

Additional Examples

A. Compound 12 and Intermediates

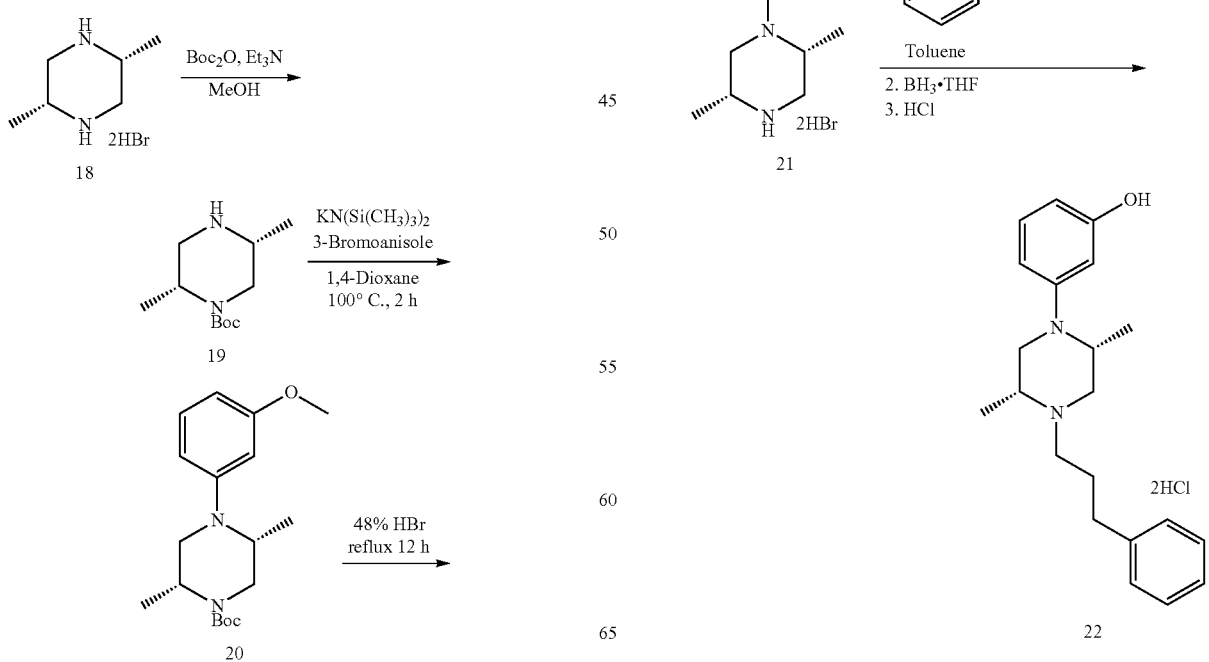

(2R,5R)-1-tert-butoxycarbonyl-2,5-dimethylpiperazine (19)

A solution of 1.43 g (5.19 mmol) of (2R,5R)-2,5-dimethyl piperazine dihydrobromide 18[1] was dissolved in 30 mL of MeOH along with 262 mg (2.59 mmol) of Et$_3$N. Into this solution was added 565 mg (2.59 mmol) of Boc$_2$O and the solution was stirred overnight. The solution was subjected to rotary evaporation and added 20 mL of CH$_2$Cl$_2$ and 20 ml of conc. NaHCO$_3$. The mixture was shaken thoroughly and the layers separated. The organic layer was extracted twice with conc. NaHCO$_3$ and the organic layer dried over MgSO$_4$, filtered and the solvents removed. The residue was purified by silica-gel column chromatography eluting with 2:1 CMA80: CH$_2$Cl$_2$ to yield 497 mg (84%) of pure 19 as a clear oil. $^1$H NMR (CDCl$_3$): δ 4.28-4.02 (bd, 1H); 3.90-3.63 (bdd, 1H); 2.99-2.94 (dd, 1H); 2.81-2.75 (d, 1H); 2.71-2.62 (m, 1H); 2.53-2.49 (d, 6H); 1.25 (d, 3H); 1.06 (d, 3H). ESIMS: m/z 215 (M+H$^+$, 100).

(2R,5R)-1-tert-butoxycarbonyl-4-(3-methoxyphenyl)-2,5-dimethylpiperazine (20)

General procedure b. was employed using 546 mg (2.55 mmol) of Boc-piperazine 19g to obtain, after chromatography, 515 mg (63%) of 20 as a yellow oil. $^1$H NMR (CDCl$_3$): δ 7.17 (t, 1H, J=9 Hz); 6.52 (d, 1H); 6.47-6.45 (m, 1H); 4.15 (q, 1H, J=6 Hz); 4.03-3.98 (m, 1H); 3.41 (m, 1H); 3.30 (dd, 1H, J$_a$=6 Hz, J$_b$=12 Hz); 2.97-2.90 (dd, 1H, J$_a$=6 Hz J$_b$=12 Hz); 2.84 (dd, 1H J$_a$=12 Hz, J$_b$=3 Hz); 1.45 (s, 9H); 1.32 (d, 3H, J=6 Hz); 1.04 (d, 3H, J=6 Hz). ESIMS: m/z 321 (M+H$^+$, 50).

(2R,5R)-3-(2,5-dimethylpiperazin-1-yl)phenol (21)

General procedure d. was employed using 515 mg (1.61 mmol) of 20 and 10 mL of conc. HBr. The dihydrobromide salt was dissolved in MeOH, stirred over 200 mg of NaHCO$_3$ for 10 minutes and then filtered. The solution was concentrated under reduced pressure and the crystallized from MeOH/Et$_2$O to yield 407 mg (69%) of 21e as a white solid: mp>220° C. $^1$H NMR (CDCl$_3$): δ 7.10 (q, 1H); 6.52 (m, 1H); 6.45 (s, 1H); 6.41 (m, 1H); 4.23 (m, 2H); 3.89-3.39 (m, 4H); 3.03 (dd, 2H); 1.45 (d, 3H, J=6 Hz); 1.15 (d, 3H, J=6 Hz). ESIMS: m/z 207 (M+H$^+$, 100).

3-[(2R,5R)-2,5-Dimethyl-4-(3-phenylpropyl)piperazin-1-yl]phenol dihydrochloride (22)

General procedure f. was employed using 300 mg (0.225 mmol) of 21. The dihydrochloride was prepared by addition of a 2 M HCl solution in EtOH and rotary evaporation. The crude HCl salt was recrystallized from EtOH/Et$_2$O to afford 260 mg (80%) of 22 as a white crystalline solid. MP>220° C. (dec). $^1$H NMR (CD$_3$OD): δ 7.26-7.19 (m, 4H); 7.07 (m, 1H); 6.62 (m, 1H); 6.45 (d, 1H, J=9 Hz); 6.37-6.33 (m, 2H); 4.26 (m, 1H); 3.58-3.30 (m, 4H); 3.22-3.03 (m, 2H); 2.75 (t, 2H, J=5 Hz); 2.20-2.01 (m, 2H); 1.50 (d, 1H, J=6 Hz); 1.42 (d, 2H, J=6 Hz); 1.14 (d, 2H, J=6 Hz); 0.97 (d, 1H, J=6 Hz). ESIMS: m/z 325 (M+H$^+$, 100). [α]$_D^{25}$ –12.3° (c 1, MeOH).

B. Process for the Preparation of Alkylpiperazines

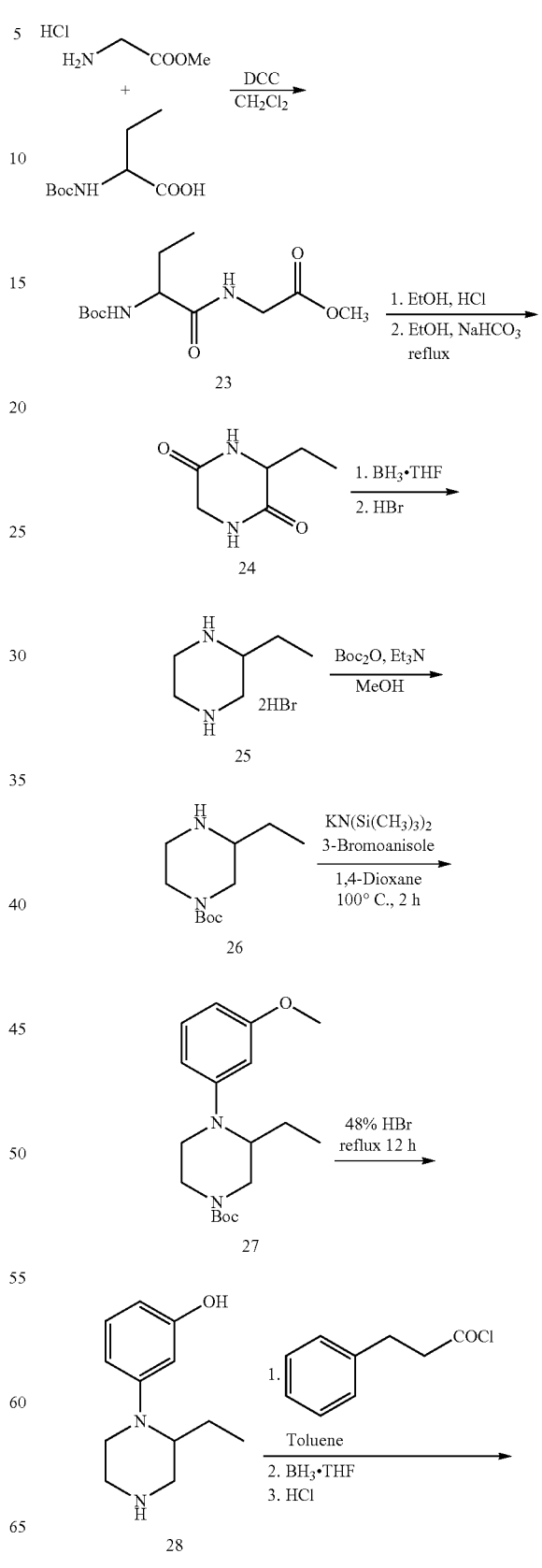

2-Ethyl-piperazine (25)

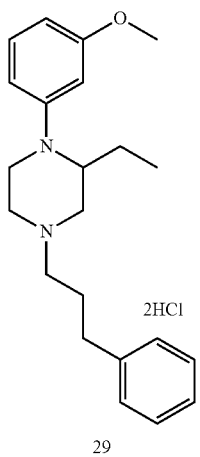

The cyclic glycine-(2-ethyl-glycine) dipeptide 23[2, 3] (0.11 g, 7.81 mmol) was suspended in 20 mL of dry THF and 31.2 mL of a 1 M solution of $BH_3$ THF were added. This mixture was stirred at reflux overnight cooled, and quenched with 10 mL of MeOH. Into this solution, 5 mL of conc. HBr were added, and the solvents were removed by rotary evaporation. The residue was recrystallized from MeOH/$Et_2O$ giving 1.08 g of the product as a white solid. The freebase was made by dissolving the salt in MeOH, stirring over $NaHCO_3$, adding $EtO_2$, filtering and removing the solvents to yield a clear oil, $^1$H NMR ($CD_3OD$): δ 30.91 (t, J=7 Hz, 3H), 1.20-1.30 (m, 2H), 2.30-3.30 (m, 7H). ESIMS: m/z 115 (M+H$^+$, 100).

1-tert-butoxycarbonyl-3-ethyl-piperazine (26)

A solution of 1.00 g (3.62 mmol) of 2-ethylpiperazine dihydrobromide 25 in 10 mL of MeOH. was cooled to 0° C. Into this flask was added 0.50 mL (3.62 mmol) of $Et_3N$ followed by a solution of 790 mg of $Boc_2O$ in 10 mL added dropwise over 4 h. The mixture was stirred for 12 h and then subjected to rotary evaporation. The remaining residue was purified by silica-gel column chromatography eluting with 1:1 CMA80:$CH_2Cl_2$ affording 700 mg of 26 as a yellow oil. $^1$H NMR ($CDCl_3$): δ 3.95 (bs, 2H); 2.97 (d, 1H, J=9 Hz); 2.77 (m, 2H); 2.48 (m, 2H); 1.46 (s, 9H); 1.40 (m, 2H); 0.95 (t, 3H, J=6 Hz) ESIMS: m/z 215 (M+H$^+$, 75); 115 (M-Boc+H$^+$, 100).

1-tert-butoxycarbonyl-3-ethyl-4-(3-methoxyphenyl) piperazine (27)

General procedure b. was employed using 0.30 g (5.35 mmol) of 26 to obtain, after chromatography, 0.20 g (44%) of 27 as a clear oil. $^1$H NMR ($CDCl_3$): δ 7.17 (t, 1H, J=9 Hz); 6.47 (dd, 1H, $J_a$=3 Hz, $J_b$=9 Hz); 6.38 (s, 1H); 4.05 (s, 2H); 3.79 (s, 3H); 3.55 (m, 1H); 3.24-3.06 (m, 4H); 1.48 (m, 11H); 0.92 (t, 3H, J=9 Hz). ESIMS: m/z 321 (M+H$^+$, 100).

3-(2-ethylpiperazin-1-yl)phenol dihydrobromide (28)

General procedure c. was employed using 200 mg (2.54 mmol) of 10c. The crude dihydrobromide was dissolved in 1 mL of MeOH stirred over $NaHCO_3$ and purified by silica-gel column chromatography eluting with 2:1 CMA80:$CH_2Cl_2$ to afford 105 mg of product was a clear oil. $^1$H NMR ($CD_3OD$): δ 7.08 (t, 1H, J=9 Hz); 6.43 (d, 1H); 6.34 (s, 1H); 6.27 (d, 1H, J=9 Hz); 3.47 (m, 1H); 3.18 (m, 1H); 3.07-2.90 (m, 5H); 1.65 (m, 1H); 1.47 (m, 1H); 0.86 (t, 3H, J=6 Hz). ESIMS: m/z 207 (M+H$^+$, 100).

3-[2-ethyl-4-(3-phenylpropyl)piperazin-1-yl]phenol dihydrochloride (29)

General procedure f. was employed using 100 mg (0.485 mmol) 10x to obtain, after salt formation, 55 mg of the dihydrochloride: mp 161-166° C. $^1$H NMR ($CD_3OD$): δ 7.35-7.15 (m, 7H); 7.12 (bs, 1H); 6.91 (bs, 1H); 4.11-3.50 (m, 5H); 2.77 (t, 2H, J=6 Hz), 2.20 (m, 2H); 1.63 (m, 2H), 0.90 (t, 3H, J=6 Hz). ESIMS: m/z 325 (M+H$^+$, 100).

C. Process for the synthesis of N-alkylamino 1-(3-hydroxyophenyl)-2-(S)-methylpiperazines

Synthesis of N-substituted (S)-3-(2-methylpiperazin-1-yl)phenols 30 and 31

Compounds bearing 4-N-substituents were synthesized in a manner similar to compounds in the trans-3,4-dimethyl-4-(3-hydroxyphenyl)piperidines reported by Thomas et al[4]. (S)-3-(2-methylpiperazin-1-yl)phenol dihydrobromide was acylated using a series of amino acids and the peptide linking reagent HBTU. Without purification, the resulting amides were reduced with $BH_3$ THF to yield the N-substituted compounds 14.

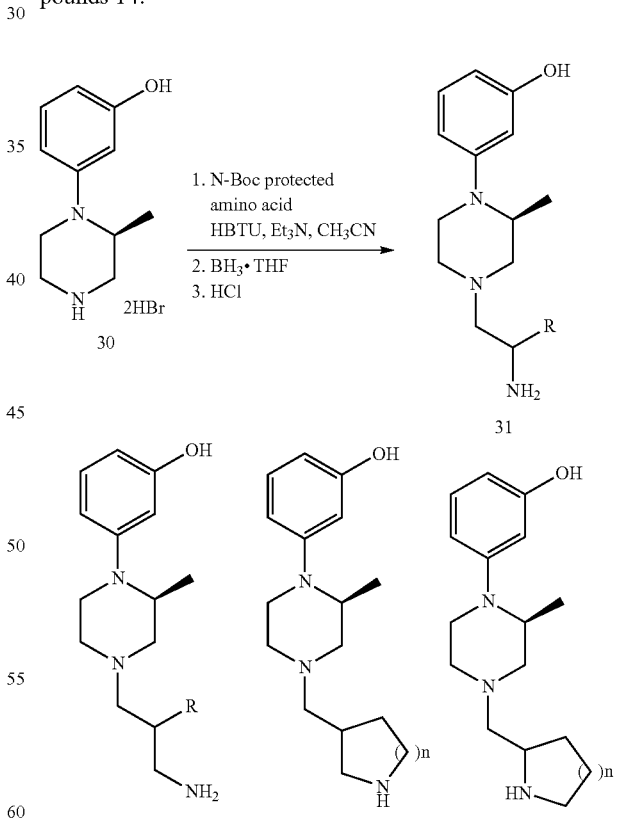

General Procedure:
Reductive Alkylation Using N-Boc-Protected Amino Acids
(S)-3-(2-methylpiperazin-1-yl)phenol dihydrobromide (100 mg, 0.282 mmol) and the N-Boc-protected amino acid (0.311 mmol) were dissolved in 1.5 mL of $CH_3CN$ and 0.12 mL (0.847 mmol) of $Et_3N$. Into this mixture was added all at once, a solution of HBTU (118 mg, 0.311 mmol) in 2 mL of CH$_3$CN. The reaction was stirred overnight. To the reaction mixture were added 0.5 mL of CH$_2$Cl$_2$ followed by 2 mL of a saturated aqueous solution of NaHCO$_3$. The mixture was shake, and the organic layer separated and washed again with 2 mL conc. NaHCO$_3$. The solvents were dried over Na$_2$SO$_4$, filtered and the solution was rotary evaporated and placed under vacuum to yield a brown foam. This material was dissolved in 2 mL of dry THF and 2 mL of a 1 M solution of BH$_3$ THF and the solution stirred for 24 h. Carefully, 0.5 mL of conc. HCl were added and the mixture was stirred for 4 h, and subjected to rotary evaporation. The residue was purified by crystallization or silica-gel column chromatography.

3-{(2S)-4-[(2-amino-ethyl]-2-methylpiperazin-1-yl}phenol (31a)

The general procedure was employed using Boc-Glycine (54 mg, 0.311 mmol). The residue was crystallized from MeOH/Et$_2$O to yield 25 mg of the product as a tan solid: mp>230° C. $^1$H NMR (CD$_3$OD): δ 7.40 (t, 1H, J=6 Hz); 7.10 (m, 2H); 6.93 (bd, 1H); 4.15 (m, 1H); 3.98-3.88 (bt, 1H); 3.75-3.68 (m, 1H); 3.60-3.50 (bd, 1H); 3.50-3.39 (bd, 1H); 3.15-3.01 (m, 2H); 1.36 (d, 3H, J=6 Hz). ESIMS: m/z 236 (M+H$^+$, 100).

3-{(2S)-4-[(2R)-2-amino-propyl]-2-methylpiperazin-1-yl}phenol (31b)

The general procedure was employed using Boc-D-Alanine (59 mg, 0.311 mmol). The residue was crystallized from MeOH/Et$_2$O to yield 55 mg of the product as a white solid: mp 210-215° C. $^1$H NMR (CD$_3$OD): δ 7.44 (t, 1H, J=6 Hz); 7.16 (m, 2H); 6.98 (m, 1H); 4.16 (bm, 1H); 3.99 (bt, 1H); 3.67 (m, 1H); 3.50-3.30 (m, 2H); 3.12-2.85 (bm, 3H); 1.36 (d, 3H, J=6 Hz); 1.17 (d, 3H, J=6 Hz). ESIMS: m/z 250 (M+H$^+$, 100).

1. Tanatani, A.; Mio, M. J.; Moore, J. S., Chain Length-Dependent Affinity of Helical Foldamers for a Rodlike Guest. *Journal of the American Chemical Society* 2001, 123, (8), 1792-1793.
2. Ognyanov, V. I.; Balan, C.; Bannon, A. W.; Bo, Y.; Dominguez, C.; Fotsch, C.; Gore, V. K.; Klionsky, L.; Ma, V. V.; Qian, Y.-X.; Tamir, R.; Wang, X.; Xi, N.; Xu, S.; Zhu, D.; Gavva, N. R.; Treanor, J. J. S.; Norman, M. H., Design of Potent, Orally Available Antagonists of the Transient Receptor Potential Vanilloid 1. Structureâˆ’Activity Relationships of 2-piperazin-1-yl-1H-benzimidazoles. *Journal of Medicinal Chemistry* 2006, 49, (12), 3719-3742.
3. Smith, G. G.; Evans, R. C.; Baum, R., Neighboring residue effects: evidence for intramolecular assistance to racemization or epimerization of dipeptide residues. *Journal of the American Chemical Society* 1986, 108, (23), 7327-7332.
4. Thomas, J. B.; Fall, M. J.; Cooper, J. B.; Rothman, R. B.; Mascarella, S. W.; Xu, H.; Partilla, J. S.; Dersch, C. M.; McCullough, K. B.; Cantrell, B. E.; Zimmerman, D. M.; Carroll, F. I., Identification of an Opioid Kappa Receptor Subtype-Selective N-Substituent for (+)-(3R,4R)-Dimethyl-4-(3-hydroxyphenyl)piperidine. *Journal of Medicinal Chemistry* 1998, 41, (26), 5188-5197.

Obviously, numerous modifications and variations of the present invention are possible in light of the above teachings. It is therefore to be understood that within the scope of the appended claims, the invention may be practiced otherwise than as specifically described herein.

REFERENCES (1) Dhawan, B. N.; Cesselin, F.; Raghubir, R.; Reisine, T.; Bradley, P. B.; Portoghese, P. S.; Hamon, M. International Union of Pharmacology. XII. Classification of opioid receptors. *Pharmacol. Rev.* 1996, 48, 567-592.
(2) Aldrich, J. V.; Vigil-Cruz, S. C. Narcotic Analgesics. In *Burger's Medicinal Chemistry and Drug Discovery*, 6th ed.; Abraham, D. J., Ed. John Wiley & Sons: New York, N.Y., 2003; Vol. 6, Chapter 7, pp 329-481.
(3) Husbands, S. M. Kappa-opioid receptor ligands. *Expert Opin. Ther. Patents* 2004, 14, 1725-1741.
(4) Prisinzano, T. E.; Tidgewell, K.; Harding, W. W. Kappa opioids as potential treatments for stimulant dependence. *AAPS J.* 2005, 7, E592-E599.
(5) Metcalf, M. D.; Coop, A. Kappa opioid antagonists: past successes and future prospects. *AAPS J.* 2005, 7, E704-E722.
(6) Carroll, F. I.; Thomas, J. B.; Dykstra, L. A.; Granger, A. L.; Allen, R. M.; Howard, J. L.; Pollard, G. T.; Aceto, M. D.; Harris, L. S. Pharmacological properties of JDTic: A novel κ-opioid receptor antagonist. *Eur. J. Pharmacol.* 2004, 501, 111-119.
(7) Thomas, J. B.; Atkinson, R. N.; Vinson, N. A.; Catanzaro, J. L.; Perretta, C. L.; Fix, S. E.; Mascarella, S. W.; Rothman, R. B.; Xu, H.; Dersch, C. M.; Cantrell, B. E.; Zimmerman, D. M.; Carroll, F. I. Identification of (3R)-7-hydroxy-N-((1S)-1-[[(3R,4R)-4-(3-hydroxyphenyl)-3,4-dimethyl-1-piperidinyl]methyl]-2-methylpropyl)-1,2,3,4-tetrahydro-3-isoquinolinecarboxamide as a novel potent and selective opioid kappa receptor antagonist. *J. Med. Chem.* 2003, 46, 3127-3137.
(8) Thomas, J. B.; Atkinson, R. N.; Rothman, R. B.; Fix, S. E.; Mascarella, S. W.; Vinson, N. A.; Xu, H.; Dersch, C. M.; Lu, Y.; Cantrell, B. E.; Zimmerman, D. M.; Carroll, F. I. Identification of the first trans-(3R,4R)-dimethyl-4-(3-hydroxyphenyl)piperidine derivative to possess highly potent and selective opioid kappa receptor antagonist activity. *J. Med. Chem.* 2001, 44, 2687-2690.
(9) Kreek, M. J.; LaForge, K. S.; Butelman, E. Pharmacotherapy of addictions. *Nat. Rev. Drug Discov.*, 2002, 1, 710-726.
(10) Zimmerman, D. M.; Nickander, R.; Horng, J. S.; Wong, D. T. New structural concepts for narcotic antagonists defined in a 4-phenylpiperidine series. *Nature* 1978, 275, 332-334.
(11) Thomas, J. B.; Mascarella, S. W.; Rothman, R. B.; Partilla, J. S.; Xu, H.; McCullough, K. B.; Dersch, C. M.; Cantrell, B. E.; Zimmerman, D. M.; Carroll, F. I. Investigation of the N-substituent conformation governing potency and μ receptor subtype-selectivity in (+)-(3R,4R)-dimethyl-4-(3-hydroxyphenyl)piperidine opioid antagonists. *J. Med. Chem.* 1998, 41, 1980-1990.
(12) Zimmerman, D. M.; Leander, J. D.; Cantrell, B. E.; Reel, J. K.; Snoddy, J.; Mendelsohn, L. G.; Johnson, B. G.; Mitch, C. H. Structure-activity relationships of the trans-3,4-dimethyl-4-(3-hydroxyphenyl)piperidine antagonists for μ and κ opioid receptors. *J. Med. Chem.* 1993, 36, 2833-2841.
(13) Mitch, C. H.; Leander, J. D.; Mendelsohn, L. G.; Shaw, W. N.; Wong, D. T.; Cantrell, B. E.; Johnson, B. G.; Reel, J. K.; Snoddy, J. D.; Takemori, A. E.; Zimmerman, D. M. 3,4-Dimethyl-4-(3-hydroxyphenyl)piperidines: Opioid antagonists with potent anorectant activity. *J. Med. Chem.* 1993, 36, 2842-2850.
(14) Zimmerman, D. M.; Gidda, J. S.; Cantrell, B. E.; Schoepp, D. D.; Johnson, B. G.; Leander, J. D. Discovery of a potent, peripherally selective trans-3,4-dimethyl-4-(3-hydroxyphenyl)piperidine opioid antagonist for the treatment of gastrointestinal motility disorders. *J. Med. Chem.* 1994, 37, 2262-2265.

(15) Delaney, C. P.; Yasothan, U.; Kirkpatrick, P. Alvimopan. *Nat Rev Drug Discov* 2008, 7, 727-8.

(16) Statnick, M. A.; Suter, T. M.; Gackenheimer, S. L.; Emmerson, P. J.; Quimby, S. J.; Gehlert, D. R.; Wheeler, W. J.; Mitch, C. H. Na+-dependent high affinity binding of [3H]LY515300, a 3,4-dimethyl-4-(3-hydroxyphenyl)piperidine opioid receptor inverse agonist. *Eur. J. Pharmacol.* 2003, 482, 139-50.

(17) Thomas, J. B.; Fall, M. J.; Cooper, J. B.; Rothman, R. B.; Mascarella, S. W.; Xu, H.; Partilla, J. S.; Dersch, C. M.; McCullough, K. B.; Cantrell, B. E.; Zimmerman, D. M.; Carroll, F. I. Identification of an opioid κ receptor subtype-selective N-substituent for (+)-(3R,4R)-dimethyl-4-(3-hydroxyphenyl)piperidine. *J. Med. Chem.* 1998, 41, 5188-5197.

(18) Beardsley, P. M.; Howard, J. L.; Shelton, K. L.; Carroll, F. I. Differential effects of the novel kappa opioid receptor antagonist, JDTic, on reinstatement of cocaine-seeking induced by footshock stressors vs cocaine primes and its antidepressant-like effects in rats. *Psychopharmacology (Berl)* 2005, 183, 118-126.

(19) Knoll, A. T.; Meloni, E. G.; Thomas, J. B.; Carroll, F. I.; Carlezon, W. A., Jr. Anxiolytic-Like Effects of κ-Opioid Receptor Antagonists in Models of Unlearned and Learned Fear in Rats. *J. Pharmacol. Exp. Ther.* 2007, 323, 838-845.

(20) Komoto, T.; Okada, T.; Sato, S.; Niino, Y.; Oka, T.; Sakamoto, T. New mu-opioid receptor agonists with piperazine moiety. *Chem. Pharm. Bull. (Tokyo)* 2001, 49, 1314-1320.

(21) Mague, S. D.; Pliakas, A. M.; Todtenkopf, M. S.; Tomasiewicz, H. C.; Zhang, Y.; Stevens, W. C., Jr.; Jones, R. M.; Portoghese, P. S.; Carlezon, W. A., Jr. Antidepressant-like effects of kappa-opioid receptor antagonists in the forced swim test in rats. *J. Pharmacol. Exp. Ther.* 2003, 305, 323-330.

(22) McLaughlin, J. P.; Marton-Popovici, M.; Chavkin, C. Kappa opioid receptor antagonism and prodynorphin gene disruption block stress-induced behavioral responses. *J. Neurosci.* 2003, 23, 5674-5683.

(23) Redila, V. A.; Chavkin, C. Stress-induced reinstatement of cocaine seeking is mediated by the kappa opioid system. *Psychopharmacology (Berl)* 2008, 200, 59-70.

(24) Carey, A. N.; Borozny, K.; Aldrich, J. V.; McLaughlin, J. P. Reinstatement of cocaine place-conditioning prevented by the peptide kappa-opioid receptor antagonist arodyn. *Eur. J. Pharmacol.* 2007, 569, 84-89.

(25) Walker, B. M.; Koob, G. F. Pharmacological evidence for a motivational role of κ-opioid systems in ethanol dependence. *Neuropsychopharmacology* 2007, 1-10.

(26) Bodnar, R. J.; Glass, M. J.; Ragnauth, A.; Cooper, M. L. General, mu and kappa opioid antagonists in the nucleus accumbens alter food intake under deprivation, glucoprivic and palatable conditions. *Brain Res.* 1995, 700, 205-212.

(27) Bortolato, M.; Aru, G. N.; Frau, R.; Orru, M.; Fa, M.; Manunta, M.; Puddu, M.; Mereu, G.; Gessa, G. L. Kappa opioid receptor activation disrupts prepulse inhibition of the acoustic startle in rats. *Biol. Psychiatry* 2005, 57, 1550-1558.

(28) Benesh, D. R.; Blanco-Pillado, M.-J. Preparation of 4-(5-Aminomethyl)indole-1-ylmethyl)benzamide Derivatives as Opioid Receptor Antagonists for the Treatment of Obesity, PCT Int. Appl. WO 2005 90, 303. 2005.

(29) McHardy, S.; Liras, S.; Guediche, S.; Coe, J. W. 4-Phenyl-piperidine Compounds and Their Use as Modulators of Opioid Receptors, US Patent Application Publication No. 204/0204453 A1. 2004.

The invention claimed is:

1. An opioid receptor antagonist represented by the formula (I):

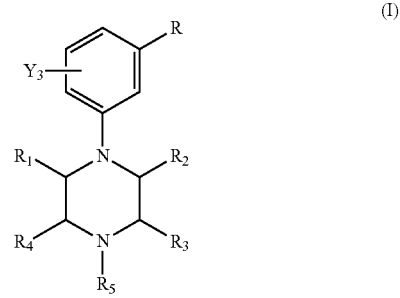

wherein

R is OH, $OC_{1-6}$ alkyl, $C_{2-8}$ alkyl, $C_{1-8}$ haloalkyl, $C_{2-8}$ alkenyl, $C_{2-8}$ alkynyl, aryl substituted by one or more groups $Y_1$, $CH_2$-aryl wherein the aryl group is substituted by one or more groups $Y_1$, $OCOC_{1-8}$ alkyl, $COC_{1-8}$ alkyl, $CONH_2$, NHCHO, $NH_2$, $NHSO_2C_{1-8}$ alkyl, or $NHCO_2C_{1-8}$ alkyl;

$Y_3$ is hydrogen, Br, Cl, F, $CF_3$, $NO_2$, $OR_8$, $CO_2R_9$, $C_{1-6}$ alkyl, $NR_{10}R_{11}$, $NHCOR_{12}$, $NHCO_2R_{12}$, $CONR_{13}R_{14}$ or $CH_2(CH_2)_nY_2$;

$R_1$, $R_2$, $R_3$ and $R_4$ are each, independently, one of the following structures:

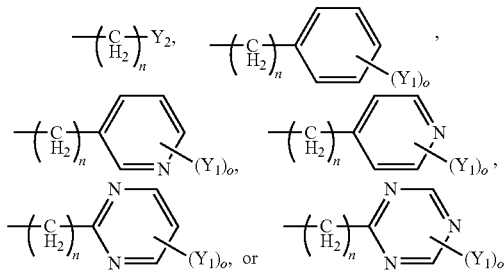

or $R_1$ and $R_2$, $R_2$ and $R_3$ and/or $R_3$ and $R_4$ are bonded together to form a cyclo alkyl group or a bridged heterocyclic ring, wherein at least one of $R_1$, $R_2$, $R_3$ and $R_4$ is other than hydrogen;

each $Y_1$ is, independently, hydrogen, OH, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$, or two adjacent $Y_1$ groups form a —O—$CH_2$—O— or —O—$CH_2CH_2$—O— group;

each $Y_2$ is, independently, hydrogen, $CF_3$, $CO_2R_9$, $C_{1-8}$ alkyl, $NR_{10}R_{11}$, $NHCOR_{12}$, $NHCO_2R_{12}$, $CONR_{13}R_{14}$, $CH_2OH$, $CH_2OR_8$, $COCH_2R_9$,

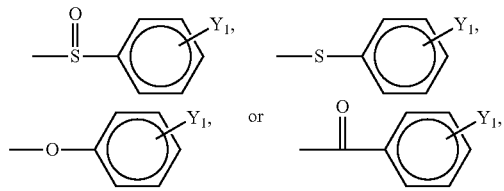

-continued

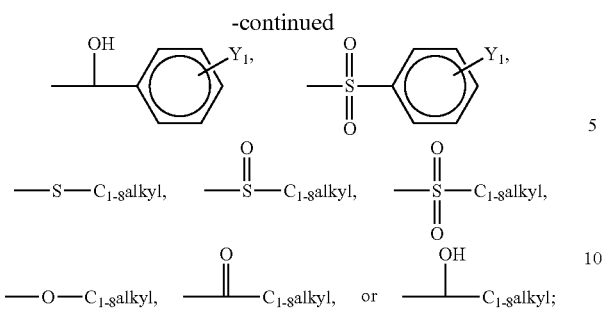

each n is, independently, 0, 1, 2 or 3;
each o is, independently, 0, 1, 2 or 3;
each $R_8$, $R_9$, $R_{10}$, $R_{11}$, $R_{12}$, $R_{13}$ and $R_{14}$ is, independently, hydrogen, $C_{1-8}$ alkyl, $CH_2$-aryl wherein the aryl group is substituted by one or more substituents OH, Br, Cl, F, CN, $CF_3$, $NO_2$, $N_3$, $C_{1-6}$ alkyl, or $CH_2(CH_2)_nY_2'$;
each $Y_2'$ is, independently, hydrogen, $CF_3$, or $C_{1-6}$ alkyl;
$R_5$ is

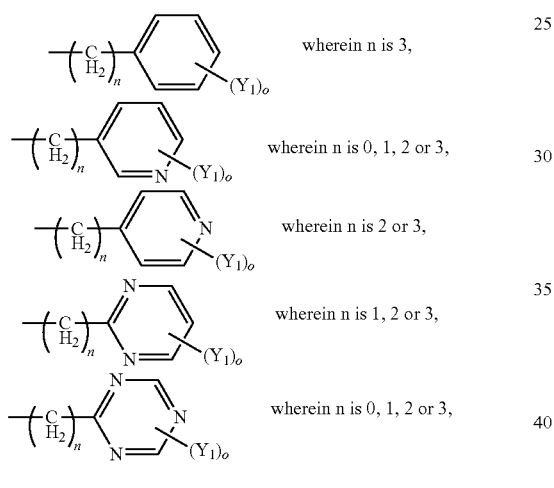

—$CH_2CH_2$—X—$R_6$, or

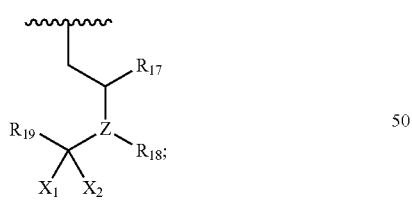

$R_6$ is $C_{2-8}$ alkenyl, $C_{1-4}$ alkyl substituted $C_{4-8}$ cycloalkyl, $C_{1-4}$ alkyl substituted $C_{4-8}$ cycloalkenyl, or thiophene;
X is a single bond, —C(O)— or —CH(OR$_{15}$)—;
$R_{15}$ hydrogen, $C_{1-6}$ alkyl, —$(CH_2)_q$-phenyl or —C(O)—$R_{16}$;
$R_{16}$ is $C_{1-4}$ alkyl or —$(CH_2)_q$-phenyl;
each q is, independently, 1, 2 or 3;
$R_{17}$ is hydrogen, $C_{1-8}$ alkyl, $CO_2C_{1-8}$ alkylaryl substituted by one or more groups $Y_1$, $CH_2$-aryl substituted by one or more groups $Y_1$, or $CO_2C_{1-8}$ alkyl;
$R_{18}$ is hydrogen, $C_{1-8}$ alkyl, $C_{2-8}$ alkenyl, $C_{3-8}$ alkynyl, $CH_2CO_2C_{1-8}$ alkyl, $CO_2C_{1-8}$ alkyl or $CH_2$-aryl substituted by one or more groups $Y_1$;

$R_{19}$ is a group selected from the group consisting of structures (a)-(p):

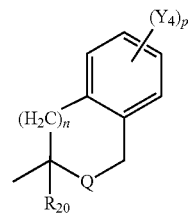
(a)

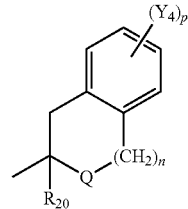
(b)

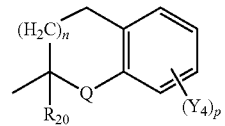
(c)

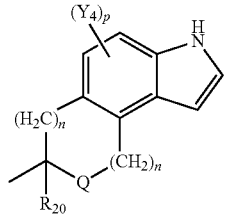
(d)

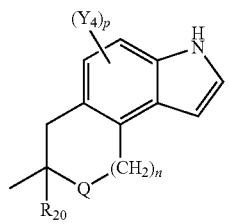
(e)

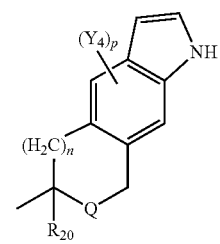
(f)

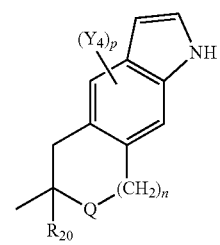
(g)

(h) 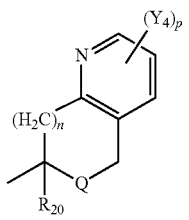

(i) 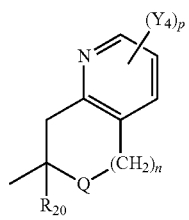

(j) 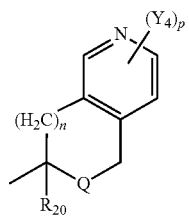

(k) 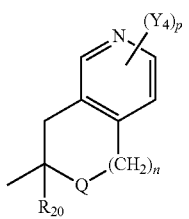

(l) 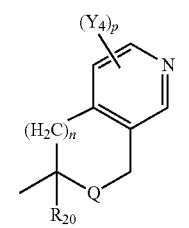

(m) 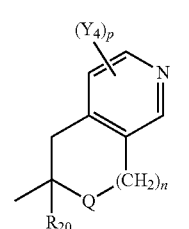

(n) 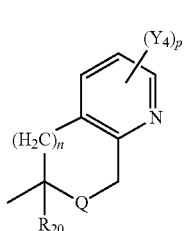

(o) 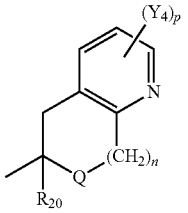

(p) 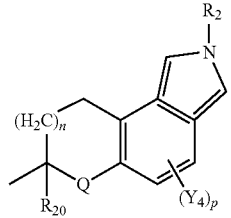

Q is $NR_{21}$, $CH_2$, O, S, SO, or $SO_2$;

each $Y_4$ is, independently, Br, Cl, F, CN, $CF_3$, $NO_2$, $N_3$, $OR_{22}$, $CO_2R_{23}$, $C_{1-6}$ alkyl, $NR_{24}R_{25}$, $NHCOR_{26}$, $NHCO_2R_{27}$, $CONR_{28}R_{29}$, or $CH_2(CH_2)_nY_2$, or two adjacent $Y_4$ groups form a —O—$CH_2$—O— or —O—$CH_2CH_2$—O— group;

p is 0, 1, 2, or 3;

$R_{20}$ is hydrogen, $C_{1-8}$ alkyl, $C_{2-8}$ alkenyl, $C_{2-8}$ alkenyl, $CH_2OR_{30}$, or $CH_2$-aryl substituted by one or more substituents $Y_1$;

each $R_{21}$ is, independently, hydrogen, $C_{1-8}$ alkyl, $CH_2$-aryl substituted by one or more substituents $Y_1$, $NR_{31}R_{32}$, $NHCOR_{33}$, $NHCO_2R_{34}$, $CONR_{35}R_{36}$, $CH_2(CH_2)_nY_2$, or C(=NH)$NR_{37}R_{38}$;

$R_{30}$ is hydrogen $C_{1-8}$ alkyl, $C_{2-8}$ alkenyl, $C_{2-8}$ alkenyl, $CH_2O_2C_{1-8}$ alkyl, $CO_2C_{1-8}$ alkyl, or $CH_2$-aryl substituted by one or more substituents $Y_1$;

$R_{22}$, $R_{23}$, $R_{24}$, $R_{25}$, $R_{26}$, $R_{27}$, $R_{28}$, $R_{29}$, $R_{31}$, $R_{32}$, $R_{33}$, $R_{34}$, $R_{35}$, $R_{36}$, $R_{37}$ and $R_{38}$ are, independently, hydrogen, $C_{1-8}$ alkyl, $CH_2$-aryl substituted by one or more substituents OH, Br, Cl, F, CN, $CF_3$, $NO_2$, $N_3$, $C_{1-6}$ alkyl, or $CH_2(CH_2)_nY_2'$;

Z is N or S, wherein when Z is S, there is no $R_{18}$;

$X_1$ is hydrogen, $C_{1-8}$ alkyl, $C_{2-8}$ alkenyl, or $C_{2-8}$ alkynyl;

$X_2$ is hydrogen, $C_{1-8}$ alkyl, $C_{2-8}$ alkenyl, or $C_{2-8}$ alkynyl;

or $X_1$ and $X_2$ together form =O, =S, or =NH;

or a pharmaceutically acceptable salt thereof.

2. The opioid receptor antagonist of claim 1, wherein R is OH, $OC_{1-3}$ alkyl, $C_{1-4}$ alkyl, $C_{1-4}$ haloalkyl, $C_{2-4}$ alkenyl, $C_{2-4}$ alkynyl, aryl substituted by one or more groups $Y_1$, $CH_2$-aryl wherein the aryl group is substituted by one or more groups $Y_1$, $OCOC_{1-4}$ alkyl, $COC_{1-4}$ alkyl, $CONH_2$, NHCHO, $NH_2$, $NHSO_2C_{1-4}$ alkyl, or $NHCO_2C_{1-4}$ alkyl; and $Y_3$ is hydrogen, Br, Cl, F, $CF_3$, $NO_2$, $OR_8$, $CO_2R_9$, $C_{1-3}$ alkyl, $NR_{10}R_{11}$, $NHCOR_{12}$, $NHCO_2R_{12}$, $CONR_{13}R_{14}$ or $CH_2(CH_2)_nY_2$.

3. The opioid receptor antagonist of claim 2, wherein $R_1$, $R_2$, $R_3$ and $R_4$ are each, independently, one of the following structures:

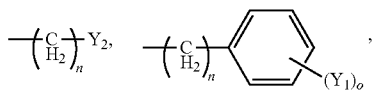

-continued

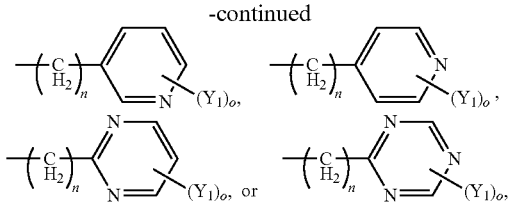

or $R_1$ and $R_2$, $R_2$ and $R_3$ and/or $R_3$ and $R_4$ are bonded together to 5 to 7 membered alkyl group or a bridged heterocyclic ring, wherein at least one of $R_1$, $R_2$, $R_3$ and $R_4$ is other than hydrogen.

4. The opioid receptor antagonist of claim 1, wherein R is OH, $OC_{1-2}$ alkyl, $C_{1-2}$ alkyl, $C_{1-2}$ haloalkyl, $C_{2-3}$ alkenyl, $C_{2-3}$ alkynyl, aryl substituted by one or more groups $Y_1$, $CH_2$-aryl wherein the aryl group is substituted by one or more groups $Y_1$, $COC_{1-2}$ alkyl, $CONH_2$, NHCHO, $NH_2$, $NHSO_2C_{1-2}$ alkyl, or $NHCO_2C_{1-2}$ alkyl.

5. The opioid receptor antagonist of claim 1, wherein R is OH, $OCH_3$, $OCF_3$, $COCH_3$, $OCOCH_3$, $CONH_2$, NHCHO, $NH_2$, $NHSO_2CH_3$, or $NHCO_2CH_3$.

6. The opioid receptor antagonist of claim 1, wherein R is OH, $OCH_3$, or $OCF_3$.

7. The opioid receptor antagonist of claim 1, wherein $Y_3$ is hydrogen.

8. The opioid receptor antagonist of claim 1, wherein $R_1$, $R_2$, $R_3$ and $R_4$ are each, independently, one of the following structures:

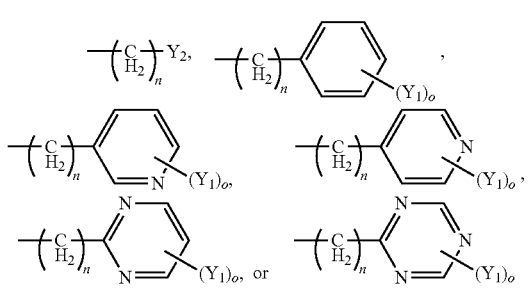

or $R_1$ and $R_2$, $R_2$ and $R_3$ and/or $R_3$ and $R_4$ are bonded together to 5 to 7 membered alkyl group or a bridged heterocyclic ring, wherein at least one of $R_1$, $R_2$, $R_3$ and $R_4$ is other than hydrogen.

9. The opioid receptor antagonist of claim 1, wherein $R_1$, $R_2$, $R_3$ and $R_4$ are each, independently, hydrogen, methyl or ethyl, wherein at least one of $R_1$, $R_2$, $R_3$ and $R_4$ is other than hydrogen.

10. The opioid receptor antagonist of claim 1, wherein $R_1$, $R_2$, $R_3$ and $R_4$ are each, independently, hydrogen or methyl, wherein at least one of $R_1$, $R_2$, $R_3$ and $R_4$ is methyl.

11. The opioid receptor antagonist of claim 1, wherein $R_1$, $R_2$, $R_3$ and $R_4$ are each, independently, hydrogen or methyl, wherein at least one of $R_1$, $R_2$, $R_3$ and $R_4$ is methyl.

12. The opioid receptor antagonist of claim 1, wherein
R is OH, $OCH_3$, or $OCF_3$;
$Y_3$ is hydrogen; and
$R_1$, $R_2$, $R_3$ and $R_4$ are each, independently, hydrogen, methyl or ethyl, wherein at least one of $R_1$, $R_2$, $R_3$ and $R_4$ is other than hydrogen; and
$R_5$ is —$(CH_2)_n$-phenyl, wherein n is 3.

13. The opioid receptor antagonist of claim 1, wherein $R_2$ is other than hydrogen as defined above.

14. The opioid receptor antagonist of claim 13, wherein $R_2$ is $C_{1-8}$ alkyl.

15. The opioid receptor antagonist of claim 13, wherein $R_2$ is methyl or ethyl.

16. The opioid receptor antagonist of claim 13, wherein $R_2$ is methyl.

17. The opioid receptor antagonist of claim 1, wherein $R_5$ is

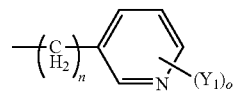

wherein n is 0, 1, 2 or 3.

18. The opioid receptor antagonist of claim 1, wherein $R_5$ is

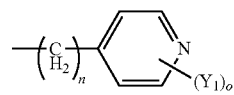

wherein n is 2 or 3.

19. The opioid receptor antagonist of claim 1, wherein $R_5$ is

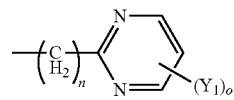

wherein n is 1, 2 or 3.

20. The opioid receptor antagonist of claim 13, wherein $R_5$ is

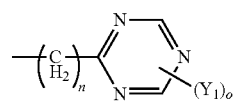

wherein n is 0, 1, 2 or 3.

21. The opioid receptor antagonist of claim 1, wherein $R_5$ is —$CH_2CH_2$—X—$R_6$.

22. The opioid receptor antagonist of claim 1, wherein $R_5$ is

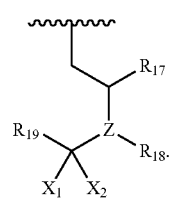

23. A pharmaceutical composition, comprising the opioid receptor antagonist of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 9,273,027 B2 | Page 1 of 1 |
| APPLICATION NO. | : 13/574179 | |
| DATED | : March 1, 2016 | |
| INVENTOR(S) | : Frank Ivy Carroll et al. | |

It is certified that error appears in the above-identified patent and that said Letters Patent is hereby corrected as shown below:

Specification

In Column 17, Line 45
"1-tort-Butoxycarbonyl-4-(3-methoxyphenyl)piperazine (8a)" should read
--1-tert-Butoxycarbonyl-4-(3-methoxyphenyl)piperazine (8a)--.

In Column 25, Line 45
"...pressure and the crystallized from" should read
--...pressure and then crystallized from--.

Claims

In Column 37, Line 64, claim 12
"...at least one of $R_1$, $R_7$, $R_1$ and $R_4$" should read
--...at least one of $R_1$, $R_2$, $R_3$ and $R_4$--.

Signed and Sealed this
Nineteenth Day of July, 2016

Michelle K. Lee
*Director of the United States Patent and Trademark Office*